United States Patent
Kogure et al.

(10) Patent No.: US 9,872,654 B2
(45) Date of Patent: Jan. 23, 2018

(54) MEDICAL IMAGE PROCESSING APPARATUS AND X-RAY CT APPARATUS

(71) Applicant: Toshiba Medical Systems Corporation, Otawara-shi (JP)

(72) Inventors: Nakaba Kogure, Zama (JP); Tomoya Kodama, Kawasaki (JP); Shinichiro Koto, Kokubunji (JP); Wataru Asano, Yokohama (JP); Hiroaki Nakai, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 49 days.

(21) Appl. No.: 14/754,969

(22) Filed: Jun. 30, 2015

(65) Prior Publication Data
US 2015/0374313 A1 Dec. 31, 2015

(30) Foreign Application Priority Data

Jun. 30, 2014 (JP) ................. 2014-134299

(51) Int. Cl.
| | |
|---|---|
| *G06K 9/00* | (2006.01) |
| *A61B 6/03* | (2006.01) |
| *A61B 6/00* | (2006.01) |
| *G06T 9/00* | (2006.01) |
| *H04N 19/15* | (2014.01) |
| *H04N 19/63* | (2014.01) |

(Continued)

(52) U.S. Cl.
CPC .......... *A61B 6/032* (2013.01); *A61B 6/5205* (2013.01); *G06T 9/00* (2013.01); *H04N 19/12* (2014.11); *H04N 19/124* (2014.11); *H04N 19/15* (2014.11); *H04N 19/17* (2014.11); *H04N 19/436* (2014.11); *H04N 19/593* (2014.11); *H04N 19/63* (2014.11)

(58) Field of Classification Search
None
See application file for complete search history.

(56) References Cited

U.S. PATENT DOCUMENTS

| | | |
|---|---|---|
| 5,978,511 A | 11/1999 | Horiuchi et al. |
| 8,532,401 B2 | 9/2013 | Kato et al. |

(Continued)

FOREIGN PATENT DOCUMENTS

| | | |
|---|---|---|
| JP | 07(1995)-298258 | 11/1995 |
| JP | 10(1998)-056640 | 2/1998 |

(Continued)

OTHER PUBLICATIONS

Japanese Office Action dated Dec. 12, 2017 in Japanese Patent Application No. 2014-134299.

*Primary Examiner* — Atiba O Fitzpatrick
(74) *Attorney, Agent, or Firm* — Oblon, McClelland, Maier & Neustadt, L.L.P.

(57) ABSTRACT

A medical image processing apparatus according to an embodiment includes compressing circuitry. The compressing circuitry is configured to compress, for each of a first data group and a second data group both of which being included in data pertaining to a medical image, each of the first data group and the second data group separately, starting from data corresponding to a boundary between the first data group and the second data group and shifting sequentially to a direction away from the boundary.

17 Claims, 21 Drawing Sheets

(51) Int. Cl.
*H04N 19/593* (2014.01)
*H04N 19/12* (2014.01)
*H04N 19/124* (2014.01)
*H04N 19/17* (2014.01)
*H04N 19/436* (2014.01)

(56) References Cited

U.S. PATENT DOCUMENTS

| | | | |
|---|---|---|---|
| 9,111,345 B2 | 8/2015 | Sato et al. | |
| 9,149,240 B2 | 10/2015 | Nakai et al. | |
| 2008/0231910 A1* | 9/2008 | Gering | H04N 19/176 |
| | | | 358/448 |
| 2009/0169119 A1 | 7/2009 | Wegener | |
| 2010/0220792 A1* | 9/2010 | Kamito | H04N 19/176 |
| | | | 375/240.25 |

FOREIGN PATENT DOCUMENTS

| | | |
|---|---|---|
| JP | 10-145590 A | 5/1998 |
| JP | 2005-261839 A | 9/2005 |
| JP | 2009111691 | 5/2009 |
| JP | 2010-17274 A | 1/2010 |
| JP | 2013-13687 A | 1/2013 |
| WO | WO 2013/076930 A1 | 5/2013 |

\* cited by examiner

INPUT DATA → COMPRESSION → OUTPUT DATA

□ : RATE GUARANTEED UNIT

MEDICAL IMAGE PROCESSING APPARATUS AND X-RAY CT APPARATUS

CROSS-REFERENCE TO RELATED APPLICATION(S)

This application is based upon and claims the benefit of priority from Japanese Patent Application No. 2014-134299, filed on Jun. 30, 2014; the entire contents of which are incorporated herein by reference.

FIELD

Embodiments described herein relate generally to a medical image processing apparatus and an X-ray Computed Tomography (CT) Apparatus.

BACKGROUND

In recent years, X-ray Computed Tomography (CT) apparatuses are configured to be able to obtain tomography images having a high level of precision by varying X-ray radiation angles with fine granularity and by introducing an X-ray detector in which X-ray detecting elements are arranged with a high density. Due to the endeavor to obtain tomography images having a high level of precision, the resolution of X-ray projection data becomes higher, the number of images taken per time period increases, and the costs of data storage and data transfer thus become higher. For this reason, X-ray CT apparatuses are configured to suppress the data increase by compressing data related to medical images, such as X-ray detection data.

Further, X-ray CT apparatuses have been developed to adopt a multi-slice system and to achieve a higher speed. To realize the multi-slice system and to achieve a higher speed, it is necessary to process a large amount of data in a real-time manner. To compress the large amount of data in a real-time manner, it is necessary to divide the data into a plurality of pieces and to compress the pieces of data in a parallel manner.

However, when data related to a medical image is divided into pieces and compressed in such a manner that the medical image is divided into two areas, the pixel values may be discontinuous across the boundary of the division. Thus, there is a possibility that the image quality may be found degraded when the pieces of data compressed in parallel are combined together and reconstructed.

DETAILED DESCRIPTION

Figure 1:
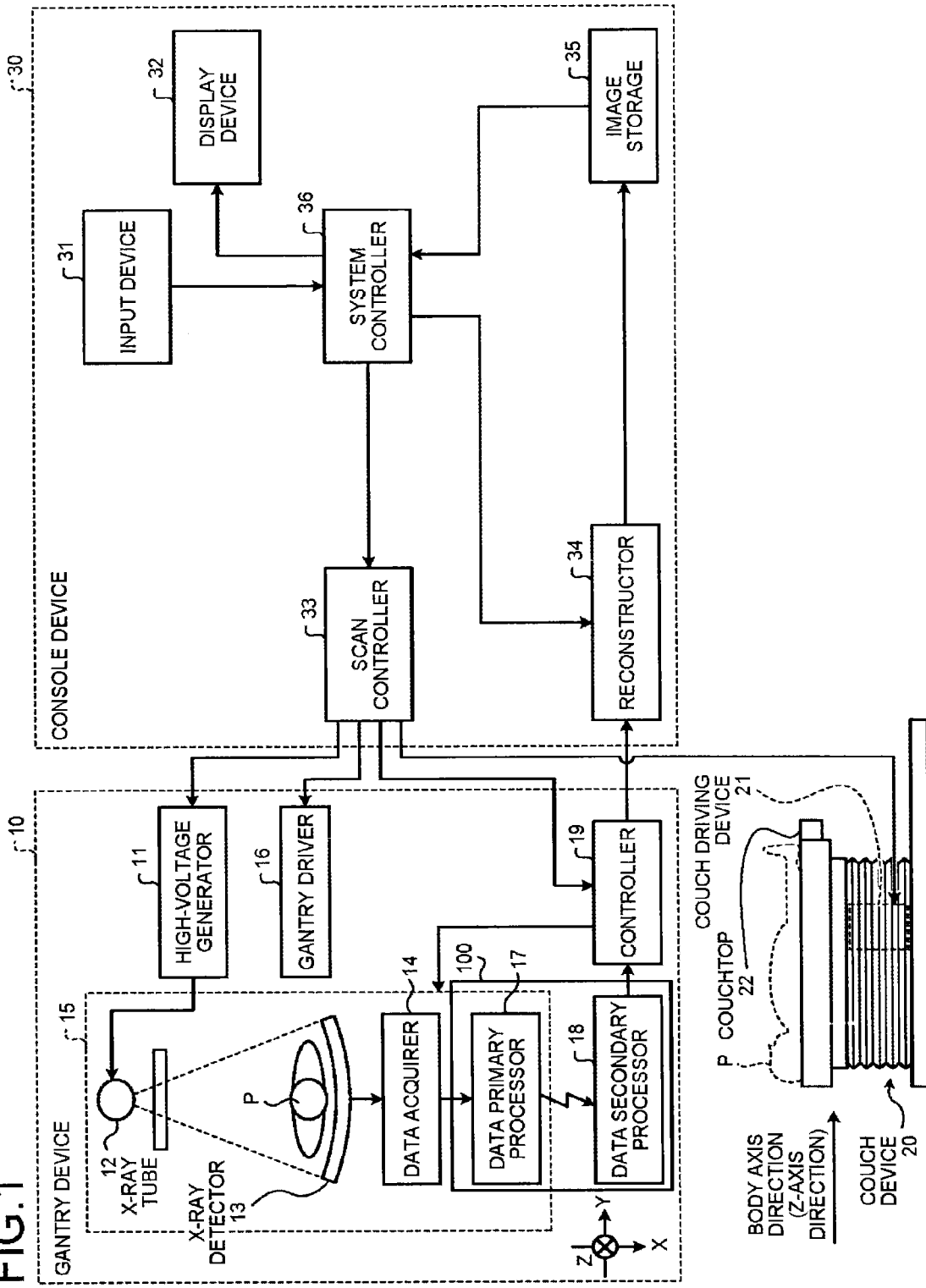
FIG. 1 is an overall diagram of an X-ray CT apparatus according to a first embodiment.

A medical image processing apparatus according to an embodiment includes compressing circuitry. The compressing circuitry is configured to compress, for each of a first data group and a second data group both of which being included in data pertaining to a medical image, each of the first data group and the second data group separately, starting from data corresponding to a boundary between the first data group and the second data group and shifting sequentially to a direction away from the boundary.

Exemplary embodiments of a medical image processing apparatus and an X-ray CT apparatus will be explained below in detail, with reference to the accompanying drawings. In the following sections, an X-ray CT apparatus that includes a medical image processing apparatus will be explained as embodiments. In the following explanation, some of the constituent elements that are the same as one another will be referred to by using the same reference characters, and duplicate explanations will be omitted.

First Embodiment

First, an overall configuration of an X-ray CT apparatus according to a first embodiment will be explained, with reference to FIG. 1. FIG. 1 is an overall diagram of an X-ray CT apparatus according to the first embodiment. As illustrated in FIG. 1, the X-ray CT apparatus according to the first embodiment includes a gantry device 10, a couch device 20, and a console device 30.

The gantry device 10 is a device configured to radiate X-rays onto an examined subject (hereinafter, "patient") P and to acquire X-ray detection data and includes a high-voltage generating unit 11, an X-ray tube 12, an X-ray detector 13, a data acquirer 14, a rotating frame 15, and a gantry driving unit 16. Further, the gantry device 10 includes a data primary processor 17 and a data secondary processor 16 configured to perform data processing on the X-ray detection data and a controller 19 configured to control the acquisition of the X-ray detection data, the data processing, and transmission to the console device 30. The X-ray tube 12, the X-ray detector 13, the data acquirer 14, and the data primary processor 17 are provided in a casing positioned on the rotated side inside the rotating frame 15 included in the gantry device 10. The high-voltage generating unit 11, the gantry driving unit 16, the data secondary processor 18, and the controller 19 are provided in a casing positioned on the fixed side outside the rotating frame 15 included in the gantry device 10.

The high-voltage generating unit 11 is a device configured to generate a high voltage and to supply the generated high voltage to the X-ray tube 12. The X-ray tube 12 is a vacuum tube configured to generate the X-rays by using the high voltage supplied from the high-voltage generating unit 11. The X-rays generated by the X-ray tube 12 are radiated onto the patient P.

The X-ray detector 13 is a detector configured to detect the X-ray detection data indicating a distribution of intensities of the X-rays that were radiated from the X-ray tube 12 and have passed through the patient P. In other words, the X-ray detector 13 obtains the X-ray detection data indicating the levels of X-ray absorption occurring inside the patient P. More specifically, the X-ray detector 13 is a two-dimensional array detector in which a plurality of rows of detecting elements are arranged along the body axis direction of the patient P (the Z-axis [slice] direction in FIG. 1), the plurality of detecting element rows each including a plurality of X-ray detecting elements arranged in the channel direction (the Y-axis direction in FIG. 1).

The rotating frame 15 is configured to support the X-ray tube 12 and the X-ray detector 13 so as to oppose each other while the patient P is interposed therebetween. The gantry driving unit 16 is a driving device configured to turn the X-ray tube 12 and the X-ray detector 13 on a circular trajectory centered on the patient P, by driving the rotating frame 15 to rotate.

The data acquirer 14 is a Data Acquisition System (DAS) and acquires the X-ray detection data detected by the X-ray detector 13. More specifically, the data acquirer 14 acquires pieces of X-ray detection data each of which corresponds to a different one of the X-ray radiation directions from the X-ray tube 12. In other words, the X-ray detection data is obtained from an X-ray detector and is obtained for each view that corresponds to a predetermined angle of an X-ray tube 12. After that, the data acquirer 14 obtains projection data by performing an amplifying process, an Analog/Digital (A/D) conversion process, and/or the like on each of the acquired pieces of X-ray detection data and outputs the obtained projection data to the data primary processor 17. In this way, the data acquirer 14 obtains projection data by acquiring X-ray detection data obtained by detecting X-rays that have passed through a subject. The X-ray detection data or the projection data is an example of data pertaining to the medical image.

The data primary processor 17 is a processor configured to perform a predetermined data processing process on the projection data. More specifically, the data primary processor 17 performs a compressing process on the projection data and transmits the compressed data to the data secondary processor 18 (explained later). Processes performed by the data primary processor 17 in the first embodiment will be explained in detail later.

The data secondary processor 18 is a processor configured to perform a data processing process to obtain the projection data by decompressing the data compressed by the data primary processor 17. Processes performed by the data secondary processor 18 in the first embodiment will be explained in detail later.

The projection data processed by the data primary processor 17 and the data secondary processor 18 is represented by the pieces of X-ray detection data that are obtained in correspondence with each of different views based on rotations angles (phases) and in correspondence with each of the X-ray detecting elements included in the X-ray detector 13, during the rotations of the X-ray tube 12 and the X-ray detector 13. Thus, the data primary processor 17 and the data secondary processor 18 are configured to perform compressing processes, transmitting processes, and decompressing processes, on the pieces of projection data that correspond to the plurality of views and that were obtained during the rotations of the X-ray tube 12 and the X-ray detector 13.

The controller 19 is configured, under control of a scan controller 33, to control the tomography image taking process performed on the patient P, by controlling operations of the rotating frame 15. Further, the controller 19 is configured to transmit the projection data resulting from the decompression by the data secondary processor 18 to the console device 30.

The couch device 20 is a device on which the patient P is placed and includes a couchtop 22 and a couch driving device 21. The couchtop 22 is a bed on which the patient P is placed. The couch driving device 21 is configured to move the patient P into the rotating frame 15, by moving the couchtop 22 in the body axis direction of the patient P (the Z-axis direction).

The console device 30 is a device configured to receive an operation performed by an operator on the X-ray CT apparatus and to reconstruct tomography images from a group of projection data acquired by the gantry device 10. The console device 30 includes an input device 31, a display device 32, the scan controller 33, a reconstructor 34, an image storage 35, and a system controller 36.

The input device 31 includes a mouse, a keyboard, a button, a trackball, a joystick, and/or the like used for inputting various types of instructions by the operator who is a medical doctor or a medical technician operating the X-ray CT apparatus. The input device 31 is configured to transfer various types of commands received from the operator to the system controller 36 (explained later).

The display device 32 includes a monitor configured to display a Graphical User Interface (GUI) used for receiving the instructions from the operator via the input device 31 and to display any of reconstructed images stored in the image storage 35 (explained later).

The scan controller 33 is configured to control operations of the high-voltage generator 11, the gantry driver 16, and the controller 19. The scan controller 33 thus controls the X-ray scan process performed by the gantry device 10 on the patient P, the acquisition process of the group of X-ray detection data, and the data processing processes performed on the group of X-ray detection data.

More specifically, the scan controller 33 performs the X-ray scan by causing X-rays to be radiated continuously or intermittently from the X-ray tube 12, while the rotating frame 15 is being rotated. For example, the scan controller 33 causes a helical scan to be performed in which images are taken by continuously rotating the rotating frame 15, while the couchtop 22 is being moved. As another example, the scan controller 33 causes a conventional scan to be performed in which images are taken by rotating the rotating frame 15 once or continuously, while the position of the patient P is fixed.

The reconstructor 34 is a processor configured to perform a reconstructing process of the tomography images (the X-ray CT images), on the basis of the projection data transmitted thereto from the controller 19. In other words, the reconstructor 34 reconstructs a tomography image of the subject on a basis of decompressed pieces of projection data decompressed by the data secondary processor 18 described later. To put it in another way, the reconstructor 34 performs the reconstruction process to generate the X-ray CT images by using the projection data received from the controller 19. The image storage 35 is configured to store therein the X-ray CT images generated by the reconstructor 34.

The system controller 36 is configured to exercise overall control of the X-ray CT apparatus by controlling operations of the gantry device 10, the couch device 20, and the console device 30. More specifically, the system controller 36 controls the acquisition process of the group of projection data performed by the gantry device 10 and the couch device 20, by controlling the scan controller 33. Further, the system controller 36 controls the compressing processes, the transmitting processes, and the decompressing processes performed on the group of projection data, by controlling the controller 19 via the scan controller 33. Further, the system controller 36 controls the image reconstructing process performed by the console device 30 by controlling the reconstructor 34. Furthermore, the system controller 36 exercises control so that any of the reconstructed images is read from the image storage 35 and displayed on the monitor included in the display device 32.

An overall configuration of the X-ray CT apparatus according to the first embodiment has thus been explained. The X-ray CT apparatus according to the first embodiment configured as described above acquires the projection data and reconstructs the X-ray CT images by using the acquired projection data.

Figure 2:
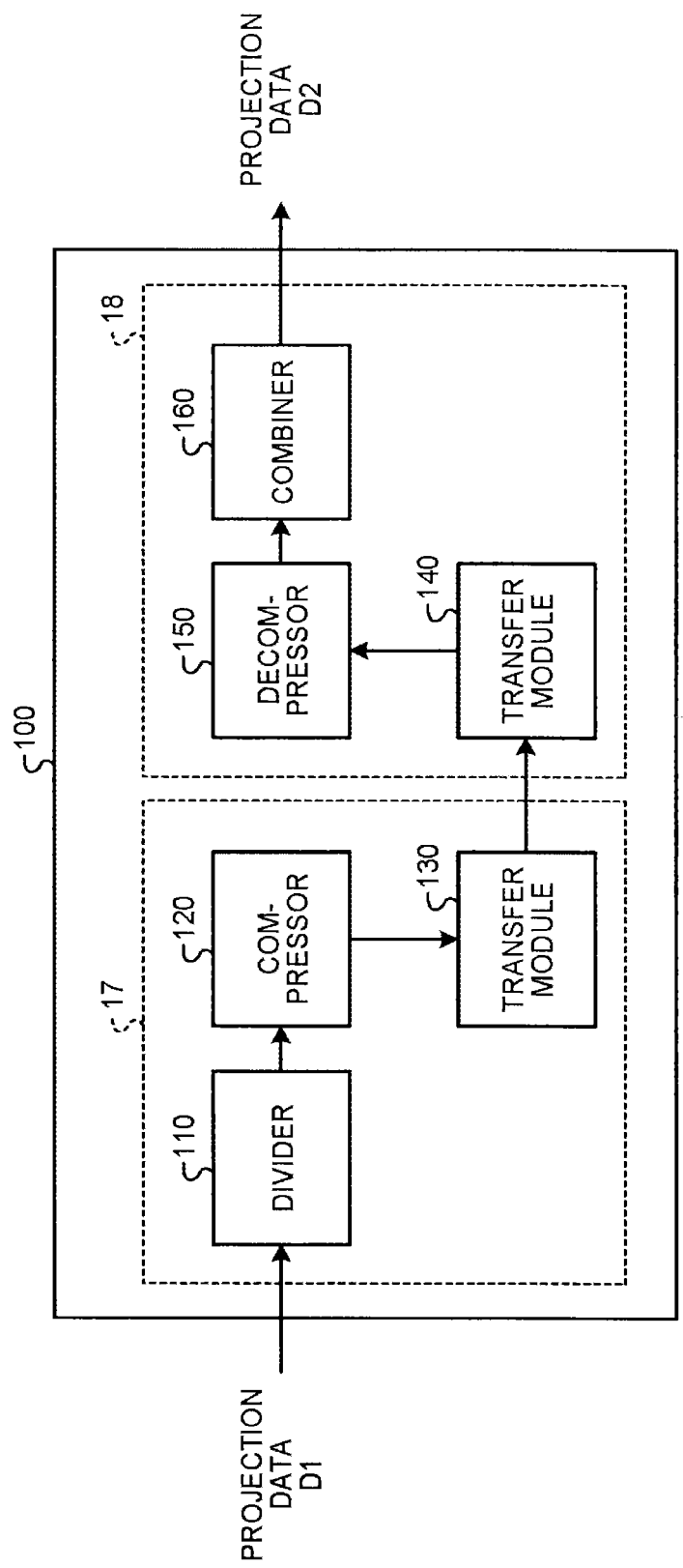
FIG. 2 is a diagram of a medical image processor according to the first embodiment.

Next, a medical image processor involving the data primary processor 17 and the data secondary processor 18 configured to process the medical images will be explained in detail. FIG. 2 is a diagram of a medical image processor 100 according to the first embodiment. As illustrated in FIG. 2, the medical image processor 100 includes a divider 110, a compressor 120, and a transfer module 130 included in the data primary processor 17, as well as a transfer module 140, a decompressor 150, and a combiner 160 included in the data secondary processor 18.

As for the X-ray CT apparatus, at first, X-rays are radiated onto the patient P, who is the subject of a medical examination, from the surrounding thereof corresponding to 360 degrees, so as to detect the level of X-ray absorption for each of the different directions and to obtain projection data D1.

The divider 110 is configured to divide the obtained projection data D1 into two pieces by using, as a boundary, a dividing line that divides the data into two areas. Specifically, the medical image processor 110 specifies a boundary to a data pertaining to a medical image and divides the data pertaining to the medical image into a first data group and a second data group at the boundary. As an example, the divider 110 adjusts or selects the boundary between the first data group and the second data group based on imaging plan information corresponding to the data pertaining to the medical image. For example, the divider 110 may adjust the boundary based on imaging plan information by performing a correction to the predetermined default position. Alternatively, the divider 110 may, based on imaging plan information, select the boundary position from predetermined boundary position candidates. It is noted that the adjustment or selection of the boundary between the first data group and the second data group may be performed by the compressor 120 or by the divider 110 under an instruction of the compressor 120. The compressor 120 is configured to compress the two pieces of projection data resulting from the division in a parallel manner. More specifically, the compressor 120 compresses the two pieces of projection data resulting from the division, sequentially starting with such parts of the detection data (which may be called "pixels") that correspond to the X-ray detecting elements and that are positioned in contact with the dividing line, in the direction away from the dividing line. To summarize, the compressor 120 compresses, for each of a first data group and a second data group both of which being included in data pertaining to a medical image, each of the first data group and the second data group separately, starting from data corresponding to a boundary between the first data group and the second data group and shifting sequentially to a direction away from the boundary. As a typical example of the data pertaining to the medical image, X-ray detection data or projection data obtained from an X-ray detector and obtained for each view that corresponds to a predetermined angle of an X-ray tube may be enumerated.

By compressing the two pieces of projection data resulting from the division in the parallel manner, the medical image processor 100 is able to generate and transfer a large amount of compressed data in a real-time manner. It is therefore possible to, for example, use the transfer bandwidth of the transfer module 130, without leaving any unused. Further, by compressing the two pieces of projection data resulting from the division, sequentially starting with such parts of the detection data that are in contact with the dividing line, in the direction away from the dividing line, the medical image processor 100 is able to prevent the detection data values from becoming discontinuous across the boundary of the division and to compress the data while inhibiting image quality deterioration of the images generated based on the detection data, because compression conditions (estimation modes) near the dividing line are equal to each other (the details will be explained later).

The transfer module 130 transfers pieces of compressed projection data. In other words, the transfer module 130 is configured to transfer the projection data that has been divided into the two pieces and compressed, to the data secondary processor 18. The transfer module 140 is configured to receive the compressed data transferred thereto from the data primary processor 17 and to output the received compressed data to the decompressor 150. As a result, the projection data is transferred from the casing positioned on the rotated side inside the rotating frame 15 to the casing on the fixed side outside the rotating frame 15. The decompressor 150 is configured to decompress the compressed data received by the transfer module 140 and to output the decompressed data to the combiner 160. In other words, the decompressor 150 decompresses compressed data of the first data group to obtain first decompressed data, and decompresses compressed data of the second data group to obtain second compressed data. The combiner 160 is configured to restore the data as projection data D2, by combining the pieces of data decompressed by the decompressor 150.

Figure 3:
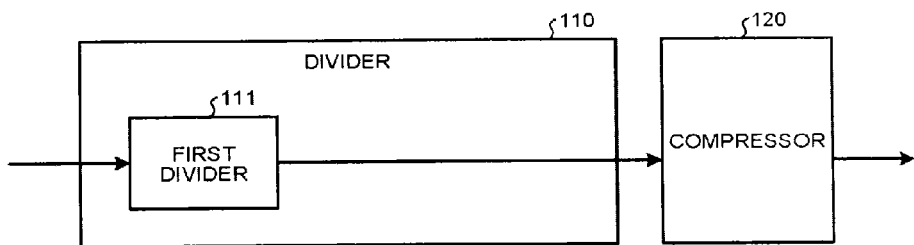
FIG. 3 is a diagram of a divider and a compressor according to the first embodiment.

FIG. 3 is a diagram of the divider 110 and the compressor 120 according to the first embodiment. As illustrated in FIG. 3, the divider 110 includes a first divider 111. The first divider 111 is configured to divide the projection data D1 into the two pieces by using the dividing line as the boundary and to output the two pieces of data to the compressor 120.

Figure 4:
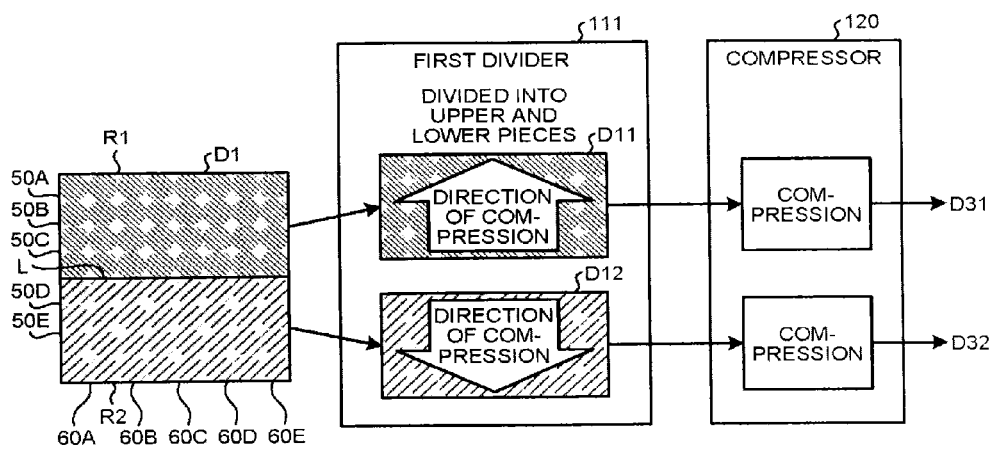
FIG. 4 is a drawing for explaining division and compression of projection data.

FIG. 4 is a drawing for explaining the division and the compression of the projection data D1. As illustrated in FIG. 4, in the projection data D1, sets of detection data (the pixels) from the X-ray detecting elements included in the two-dimensional array detector are arranged in the channel direction (the left-and-right direction in FIG. 4) and in the detector row direction (the up-and-down direction in FIG. 4). In this situation, each of the dots with hatching patterns in the projection data D1 represents detection data (a pixel) from one detector. The different hatching patterns of the dots are used to indicate whether each of the dots is divided into divided data D1 or divided data D12. Here, the position 50A is the data of the uppermost position, with the position 50B, 50C, 50D and 505 being in the descending order. The position 60A is the data of the leftmost position, with the position 60B, 60C, 60D and 605 being in order close to the left.

The first divider 111 is configured to divide the projection data D1 into the two pieces, by using the dividing line L that extends parallel to the channel direction so as to divide the data into an upper area R1 and a lower area R2. The dividing line L is the line that divides the projection data D1 into the areas R1 and R2 corresponding to the upper and the lower halves. Information about the dividing line L is configured into a memory in advance, as information about the positions of the X-ray detectors 13 (the output channels of the X-ray detectors) to be divided. The first divider 111 divides the projection data D1 along the dividing line L and generates the divided data D11 in the upper area R1 and the divided data D12 in the lower area R2. In other words, the first divider 111 performs a division of the data pertaining to the medical image data into two areas with a dividing line being the boundary and acquires the first data group and the second data group. By dividing the projection data D1 in the direction parallel to the channel direction in this way, it is possible to easily realize a data position re-arranging process or the like, during the dividing. Here, a case where the divider 111 performs a division of the data pertaining to the medical image data into two areas of upper and lower areas is explained. However, embodiments are not limited to this case. For example, the divider 111 may perform a division of the data pertaining to the medical image into two areas of left and right areas.

The compressor 120 outputs pieces of compressed data D31 and D32 by compressing the pieces of divided data D11 and D12 resulting from the division, sequentially starting with such parts of the detection data (the pixels) that are in contact with the dividing line L, in the direction away from the dividing line L (in the detector row direction). More specifically, with respect to the divided data D11, the compressor 120 generates and outputs the compressed data D31 by sequentially performing compressing processes upward, starting with such a part of the detection data (the pixels) that is in a center part of the projection data D1 and is in contact with the dividing line L so that the first line in the projection data D1 is compressed last. Similarly, with respect to the divided data D12, the compressor 120 generates and outputs the compressed data D32 by sequentially performing compressing processes downward, starting with such a part of the detection data (the pixels) that is in a center part of the projection data D1 so that the last line in the projection data D1 is compressed last. In other words, the compressor 120 compresses the first data group and the second data group, starting from the boundary and shifting sequentially to a direction away from the boundary. For example, the compressor 120 compresses, among the first data group and the second data group, a piece of data group corresponding to the upper area after the division, sequentially starting with such a part of the data that is in contact with the dividing line in an upward direction and compresses, among the first data group and the second data group, a piece of data group corresponding to the lower area after the division, sequentially starting with such a part of the data that is in contact with the dividing line in a downward direction.

In the first embodiment, the projection data D1 is divided into the upper and lower halves; however, the position of the dividing line L may be changed so as to be above the center part or below the center part. As another example, the dividing line L may be drawn so as to extend perpendicularly to the channel direction (i.e., in the detector row direction). When the dividing line L is drawn so as to extend perpendicularly to the channel direction, the projection data D1 is divided into two pieces on the left and on the right, so that compressing processes are sequentially performed, starting with such parts of the detection data (the pixels) that are in contact with the dividing line L, in the directions towards the left and the right. Further, as long as the dividing line L divides the projection data D1 into two areas R1 and R2, the dividing line L may be in a convex shape or a concave shape. Regardless of what type of dividing line L is used to obtain the pieces of divided data D11 and D12, the compressor 120 generates pieces of compressed data D31 and D32, by sequentially performing the compressing processes, starting with such parts of the detection data (the pixels) that are in contact with the dividing line L, in the direction away from the dividing line L. Further, the position and the direction of the dividing line L may be changed in accordance with the image taking site (the head, the abdomen, or the like), on the basis of an image taking plan that is used for taking images of the patient P and is input through the input device 31. For example, when images of the head are taken, the dividing line L may be drawn so as to extend perpendicularly to the channel direction, and when images of the abdomen are taken, the dividing line L may be drawn so as to extend parallel to the channel direction.

To put it in another way, when imaging information regarding a predetermined region is included in the imaging plan information corresponding to the data pertaining to the medical image data, the compressor 120 specifies the first data group and the second data group such that the boundary between the first data group and the second data group becomes perpendicular to a channel direction of an X-ray detector 13 that detects the data pertaining to the medical image data. The predetermined region is, for example, cephalic region. Here, the reason why the boundary is configured perpendicular to the channel direction when it comes to cephalic imaging is as follows: in cephalic imaging, the left or the right area that is away from the center is an "air" region that does not contribute to diagnosis, therefore an image quality degraded area (the area containing the dividing line L) may as well be translated to the "air" region that does not contribute to the diagnosis. Furthermore, the compressor 120 may perform a similar processing in a case of "arm region imaging" in which the patient P has his/her arm inserted into the opening of the bore and has the image taken. It is noted that in a case of imaging of other regions, for example, the configuration of the boundary need not be the same as described above. The compressor 120 may configure the boundary such that it is perpendicular to the channel direction or such that it is parallel to the channel direction.

For medical images that are expected to be used in diagnosis or the like, there is a demand for extremely high image quality. For this reason, the compressor 120 implements a Differential Pulse-Code Modulation (DPCM) process that prevents the image quality of the one line at the head from being lowered, thereby performing a compression. The compressing method used in the first embodiment, however, does not necessarily have to be a method using the DPCM process. It is acceptable to adopt any of various types of compressing methods (e.g., a compressing method used for a Joint Photographic Experts Group (JPEG) format).

Figure 5A:
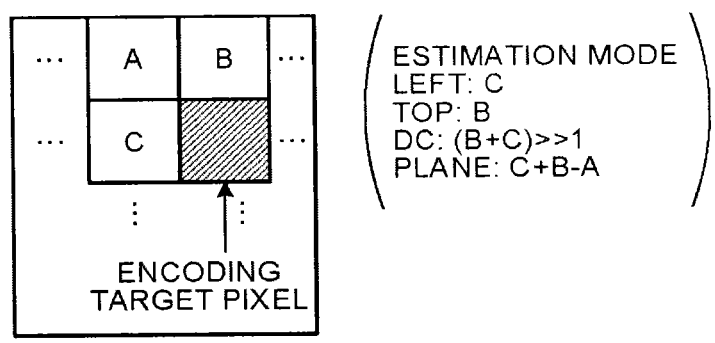
FIG. 5A and FIG. 5B are drawings for explaining estimation directions in a Differential Pulse-Code Modulation (DPCM) process.
Figure 5B:
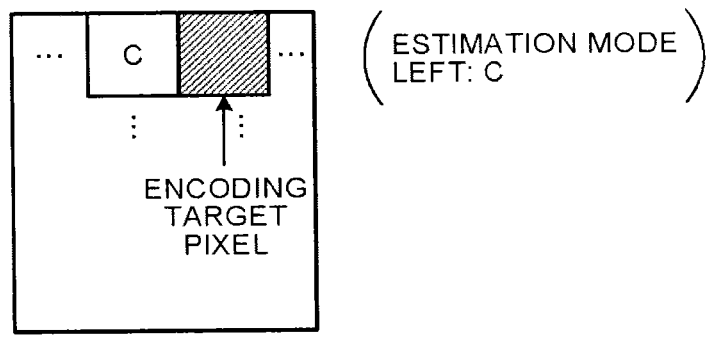
Figure 6:
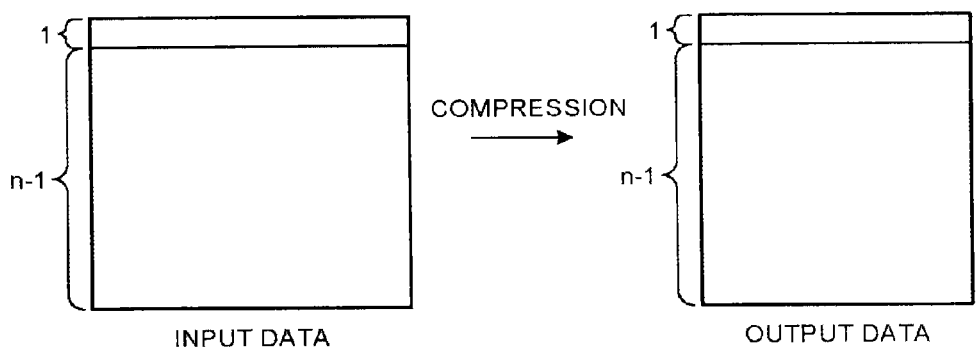
FIG. 6, FIG. 7 and FIG. 8 are drawings for explaining a method for assigning encoding amounts in the DPCM process.
Figure 7:
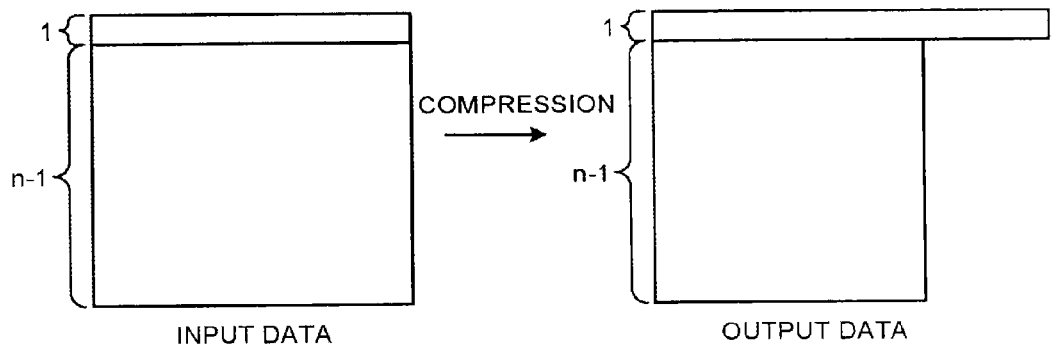
Figure 8:
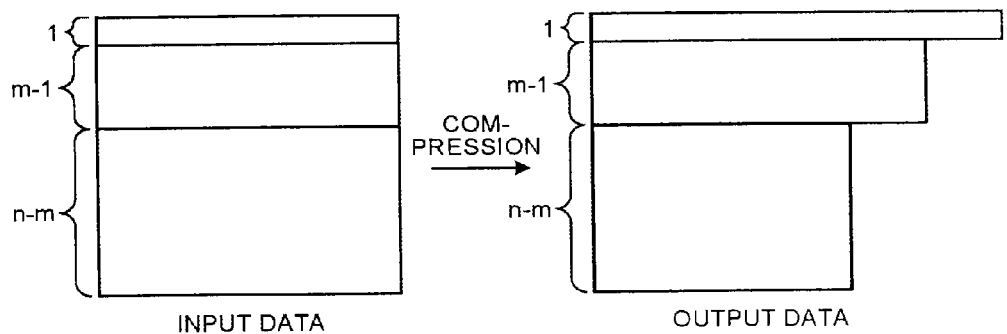

Next, the compressing method using the DPCM process that prevents the image quality of the one line at the head (hereinafter, the "head line") from being lowered will be explained. FIGS. 5A and 5B are drawings for explaining estimation directions in the DPCM process. FIGS. 6 to 8 are drawings for explaining a method for assigning encoding amounts in the DPCM process.

As illustrated in FIGS. 5A and 5B, when performing an encoding process by using the DPCM process, an encoding target pixel is encoded by making an estimation from pixels positioned adjacent to the encoding target pixel.

As illustrated in FIG. 5A, for any line other than the head line, it is possible to reduce residual signals with respect to the encoding target pixel, by selecting the most appropriate mode from among the following estimation modes: Left, Top, DC, and PLANE. Examples of calculation formulae in the estimation modes are presented in FIG. 5A. As for the DC mode, (B+C)>>1 may be used. As for the PLANE mode, C+B−A may be used.

In contrast, as illustrated in FIG. 53, because the head line does not have any line above, the estimation mode is limited to the one in the left direction. For this reason, the head line is not possible to have an efficient estimation for the encoding target pixel, and the encoding efficiency is thus lowered. In other words, if the encoding amount for each line is constant, because the image quality of the head line becomes lower than that of other lines, it may not be possible to keep the image quality uniform within the image.

FIG. 6 illustrates an example of output data obtained by assigning encoding amounts to input data (shown on the left side of FIG. 6) of which the height is n, in such a manner that the data size (the compressed size) of the head line is equal to the data size (the compressed size) of other lines corresponding to "n-l". The encoding amount for each line is illustrated in the right side of FIG. 6. In this example, because the encoding efficiency for the head line is lower than the encoding efficiency for the lines other than the head line, the image quality of the head line is degraded.

To cope with this situation, as illustrated in FIG. 7, by arranging the data size (the compressed size) of the head line to be larger than the data size (the compressed size) of other lines corresponding to "n-1", the compressor 120 is able to inhibit the image quality degradation of the head line. In other words, the compressor 120 assigns a larger encoding amount for compression of data closest to the boundary than encoding amount for compression of other data. For example, the compressor 120 assigns a larger encoding amount for compression of such a part of data corresponding to a first row that is in contact with a dividing line separating the first data group from the second data group than for compression of other parts of the data. Consequently, the image quality is kept uniform within the image, and the image quality of the entire screen is improved. Further, as the data size (the compressed size) of the head line is arranged to be larger, the image quality of the head line is enhanced. It is therefore possible to also enhance the image quality of the data of the head line.

Further, as illustrated in FIG. 8, the compressor 120 divides the input data structured with n lines (where n is an integer that is 1 or larger) into the following pieces: the head line; the lines that remain after excluding the head line from m lines at the head, which correspond to "m-1" lines at the head; and the lines other than the m lines at the head. After that, the compressor 120 arranges the data size (the compressed size) of the head line to be larger than the data size (the compressed size) of other lines and arranges the data size (the compressed size) of the remaining "m-1" lines at the head to be larger than the data size (the compressed size) of the lines other than the m lines at the head. The compressor 120 is therefore able to inhibit the image quality degradation of the head line, to keep the image quality uniform within the image, and to enhance the image quality of the entire screen. Further, because the data size (the compressed size) of the head line is arranged to be larger, the image quality of the head line is enhanced. It is therefore possible to also enhance the image quality of the data of the head line.

Figure 9:
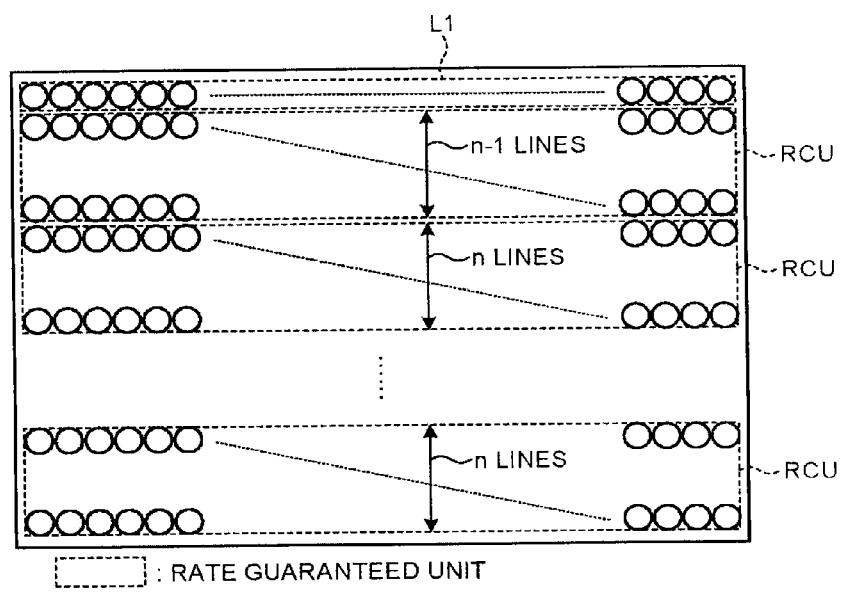
FIG. 9 is a drawing for explaining bit rate guaranteed units.

FIG. 9 is a drawing for explaining bit rate guaranteed units. As illustrated in FIG. 9, it is possible to handle one frame of the projection data D1 by using dividers each made up of n lines, by dividing the frame into: the head line; a top RCU (rate guaranteed unit) made up of "n-1" lines; and a plurality of RCUs each made up of n lines. For example, when a packetizing process (to packetize the data into collective units each made up of n lines) is performed at a stage subsequent to the compressing process, by considering the n lines made up of the head line and the top RCU (n-1 lines) as one unit, it is possible to handle the data in those n lines in the same manner as with the other RCUs each made up of n lines. In that situation, it is possible to perform the packetizing process in a well-balanced manner by setting the compression rate for the head line and the top RCU (the n-1 lines) and for the RCUs (n lines each) independently of each other.

The DPCM process to prevent the image quality of the head line from being lowered is explained above, by using the example in which the encoding amount assigned for M pixels (where M>1) in the first line according to the compression order is arranged to be larger than that for the other pixels. Alternatively, the process is applicable not only to the single line, but also to a plurality of lines.

Generally speaking, when data is divided and compressed by using an estimation based on adjacently-positioned pixels, the pixel values after the compression are found to be discontinuous because, at the boundary of the division, it is not possible to make an estimation across the boundary. The image quality of the reconstructed image is therefore degraded. To cope with this situation, by inhibiting the image quality degradation of the head line, it is possible to reduce the discontinuity at the boundary of the division. In addition, because it is possible to reduce discontinuity in the reconstructed projection data, it is possible to inhibit the image quality degradation caused by the division.

In the present example, the example in which the data is divided into two pieces is explained. When the number of pieces into which the data is divided is larger than two, the compressing processes may sequentially be performed in a similar manner while using the dividing line L described above as the center, in the direction away from the dividing line L. However, if the number of divided pieces is larger than two, there is a possibility that discontinuity may be exhibited at the dividing boundaries other than the boundary made by the dividing line L. In the embodiments described below (second, third, and fourth embodiments), examples will be explained to indicate how to cope with discontinuity at the dividing boundaries when the number of divided pieces is larger than two.

The projection data is obtained by radiating X-rays onto the subject of a medical examination from the surrounding thereof corresponding to 360 degrees (from any orientation) and detecting the level of X-ray absorption for each of the different directions. Usually, the target of the medical examination (the head, the abdomen, or the like) of the patient P is included in a center part of the projection data. Further, the target of the medical examination often includes clinically important information. For this reason, when projection data is divided at the center into upper and lower pieces and compressed starting from the center, it is possible to perform the compressing processes while enhancing the image quality of the center part, which is important, by performing the compressing processes while assigning a larger encoding amount to the head line so as to enhance the image quality of the head line.

Figure 10:
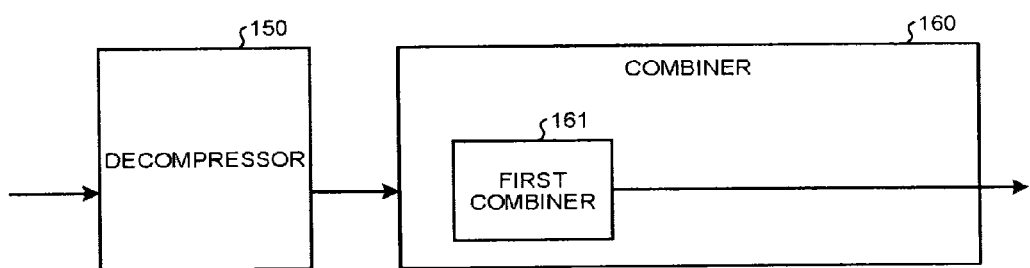
FIG. 10 is a diagram of a decompressor and a combiner according to the first embodiment.

FIG. 10 is a diagram of the decompressor 150 and the combiner 160 according to the first embodiment. As illustrated in FIG. 10, the combiner 160 includes a first combiner 161. The first combiner 161 is configured to combine the pieces of data decompressed by the decompressor 150 together so as to fit each other at the dividing line L. In other words, the first combiner 161 combines the first decompressed data and the second compressed data so as to fit each other at a dividing line corresponding to the boundary.

Figure 11:
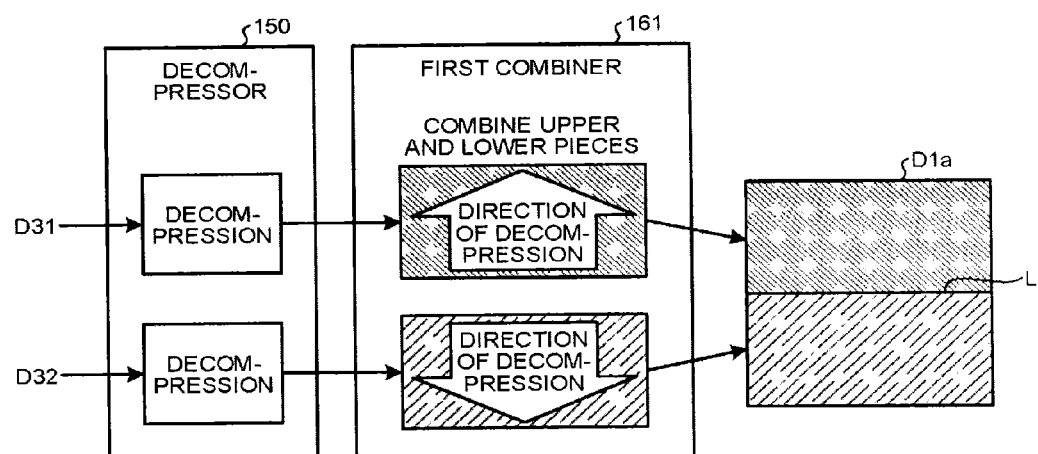
FIG. 11 is a drawing for explaining decompression and combining of compressed data.

FIG. 11 is a drawing for explaining decompression and combining of the pieces of compressed data D31 and D32. As illustrated in FIG. 11, the compressed data D31 in the upper area R1 and the compressed data D32 in the lower area R2 are each decompressed by the decompressor 150. More specifically, similarly to the compressing processes, decompressing processes are sequentially performed, starting with such parts of the detection data (the pixels) that are in contact with the dividing line L, in the direction away from the dividing line L. After that, the first combiner 161 generates and outputs projection data D1a , by combining the pieces of data decompressed by the decompressor 150 together so as to fit each other at the dividing line L. More specifically, the first combiner 161 sequentially combines the pieces of data obtained by decompressing the pieces of compressed data D31 and D32, in such a manner that, when the decompressing processes were sequentially performed starting with the lines that are in contact with the dividing line L, the last line of the data obtained by decompressing the compressed data D31 and the last line of the data obtained by decompressing the compressed data D32 are combined last. Because of this arrangement, the projection data D1a obtained as a result of the combining process has the same positional arrangement of data, as the projection D1 before the compression.

Second Embodiment

Figure 12:
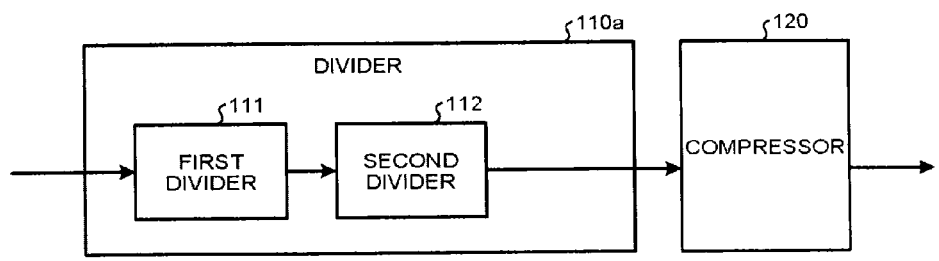
FIG. 12 is a diagram of a divider and a compressor according to a second embodiment.

FIG. 12 is a diagram of a divider 110a and a compressor 120 according to a second embodiment. As illustrated in FIG. 12, in the second embodiment, the divider 110a includes a second divider 112 subsequently to the first divider 111. The second divider 112 is configured to divide the pieces of data each of which corresponds to a different one of the two areas (R1 and R2) resulting from the division by the first divider 111, into a plurality of pieces while thinning out parts of the detection data (the pixels) alternately.

Figure 13:
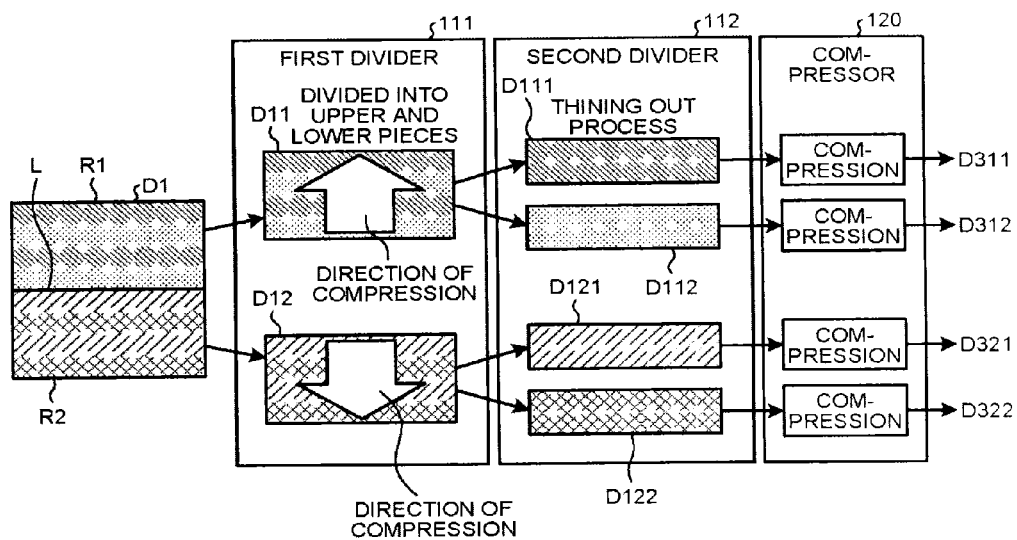
FIG. 13 is a drawing for explaining division and compression of projection data.

FIG. 13 is a drawing for explaining division and compression of the projection data D1. As illustrated in FIG. 13, the second divider 112 divides the pieces of divided data D11 and D12 resulting from the division by the first divider 111, into pieces of divided data D111, D112, D121, and D122, by thinning out parts of the data alternately, so as to increase the number of divided pieces up to four. In other words, the second divider 112 alternately thins out and divides the first data group into a plurality of pieces of data and alternately thins out and divides the second data group into a plurality of pieces of data. More specifically, the second divider 112 further divides the divided data D11 into the two pieces of divided data D111 and D112, by performing an interleaving processing on each line for the even-numbered lines and the odd-numbered lines. Similarly, the second divider 112 further divides the divided data D12 into the two pieces of divided data D121 and D122, by performing an interleaving processing on each line for the even-numbered lines and the odd-numbered lines. While using the same method, it is also acceptable to perform the interleaving processing to divide the data into pieces of which the number is larger than two.

The compressor 120 generates and outputs pieces of compressed data D311, D312, D321, and D322 by compressing the pieces of divided data D111, D112, D121, D122 resulting from the division by the second divider 112, sequentially starting with the dividing line L side, in the direction away from the dividing line L.

As explained above, when the number of divided pieces is increased, it is possible to realize an embodiment by combining the dividing process in which the parts of the detection data (the pixels) are thinned out alternately. Further, by thinning out parts of the detection data (the pixels) in the direction perpendicular to the channel direction (the horizontal direction of the projection data D1 in the present example), it is possible to easily realize a data position re-arranging process or the like during the dividing process.

For medical images that are expected to be used in diagnosis or the like, there is a demand for extremely high image quality. For this reason, the compressor 120 implements the Differential Pulse-Code Modulation (DPCM) process that prevents the image quality of the head line from being lowered. Generally speaking, when data is divided and compressed by using an estimation based on adjacently-positioned pixels, the pixel values after the compression are found to be discontinuous because, at the boundary of the division, it is not possible to make an estimation across the boundary. The image quality of the reconstructed image is therefore degraded. To cope with this situation, by performing the compressing process after the dividing process that uses the interleaving processing as described in the second embodiment, it is possible to reduce the discontinuity at the boundary of the division. Accordingly, by reducing the discontinuity in the reconstructed projection data D2, it is possible to inhibit the image quality degradation caused by the division.

Figure 14:
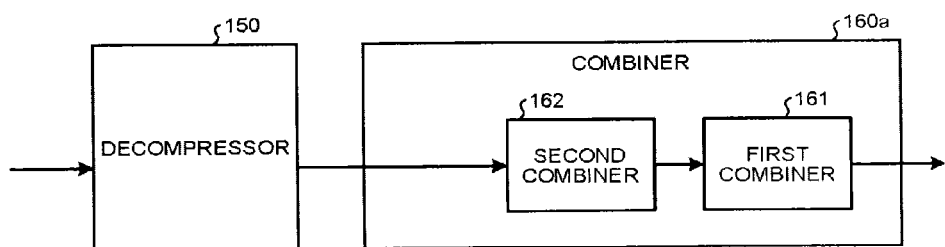
FIG. 14 is a diagram of a decompressor and a combiner according to the second embodiment.

FIG. 14 is a diagram of the decompressor 150 and a combiner 160a according to the second embodiment. As illustrated in FIG. 14, the combiner 160a includes a second combiner 162 configured to combine the pieces of data decompressed by the decompressor 150 together, prior to the first combiner 161.

Figure 15:
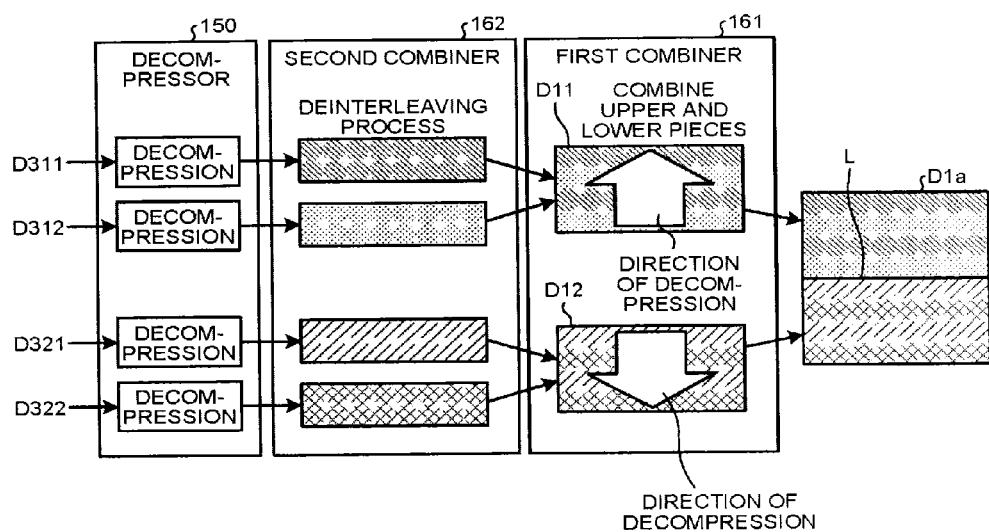
FIG. 15 is a drawing for explaining decompression and combining of compressed data.

FIG. 15 is a drawing for explaining decompression and combining of the pieces of compressed data D311, D312, D321, and D322. As illustrated in FIG. 15, the pieces of compressed data D311, D312, D321, and D322 are each decompressed by the decompressor 150. In other words, the decompressor 150 decompresses pieces of data each of which each of a plurality of divided first data is compressed into, to obtain a plurality of third decompressed data, the first data group has been alternately thinned out and divided into each of the plurality of divided first data, and the decompressor 150 decompresses pieces of data each of which each of a plurality of divided second data is compressed into, to obtain a plurality of fourth decompressed data, the second data group has been alternately thinned out and divided into each of the plurality of divided second data. More specifically, similarly to the compressing processes, the pieces of data are sequentially decompressed starting with the dividing line L side, in the direction away from the dividing line L.

The second combiner 162 is configured to combine four pieces of divided data into two pieces of divided data, by performing a deinterleaving processing on the pieces of data decompressed by the decompressor 150. More specifically, the second combiner 162 combines data decompressed by the decompressor 150, by deinterleaving processing which alternately combines parts of the detection data(pixels), to obtain the pieces of data corresponding to the upper area R1 and the lower area R2, respectively. In other words, the second combiner 162 alternately combines the plurality of third decompressed data to obtain the first decompressed data, and alternately combines the plurality of fourth decompressed data to obtain the second decompressed data. In the second embodiment, the deinterleaving processing is performed for each line for the odd-numbered lines and the even-numbered lines. In this situation, the deinterleaving processing needs to make a matching pair with the interleaving processing used by the second divider 112.

The first combiner 161 generates and outputs the projection data D1a, by combining together the pieces of data (the pieces of data corresponding to the upper area R1 and the lower area R2) resulting from the combining process by the second combiner 162 so as to fit each other at the dividing line L. More specifically, the first combiner 161 sequentially combines the pieces of decompressed data, in such a manner that, when the decompressing processes were sequentially performed starting with the lines that are in contact with the dividing line L, the last line of the data resulting from the decompression with respect to the area R1 and the last line of the data resulting from the decompression with respect to the area R2 are combined last. Because of this arrangement, the projection data D1a obtained as a result of the combining process has the same positional arrangement of data, as the projection D1 before the compression.

Third Embodiment

Figure 16:
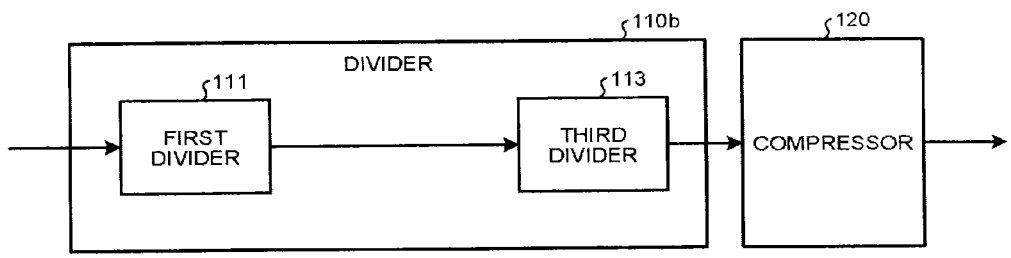
FIG. 16 is a diagram of a divider and a compressor according to a third embodiment.

FIG. 16 is a diagram of a divider 110b and the compressor 120 according to a third embodiment. As illustrated in FIG. 16, in the third embodiment, the divider 110b includes a third divider 113 subsequently to the first divider 111. The third divider 113 is configured to divide the pieces of data each of which corresponds to a different one of the two areas (R1 and R2) resulting from the division by the first divider 111, into a plurality of pieces in correspondence with mutually-different frequency bands. In other words, the third divider 113 divides the first data group into multiple different frequency bands, and divides the second data group into multiple different frequency bands.

Figure 17:
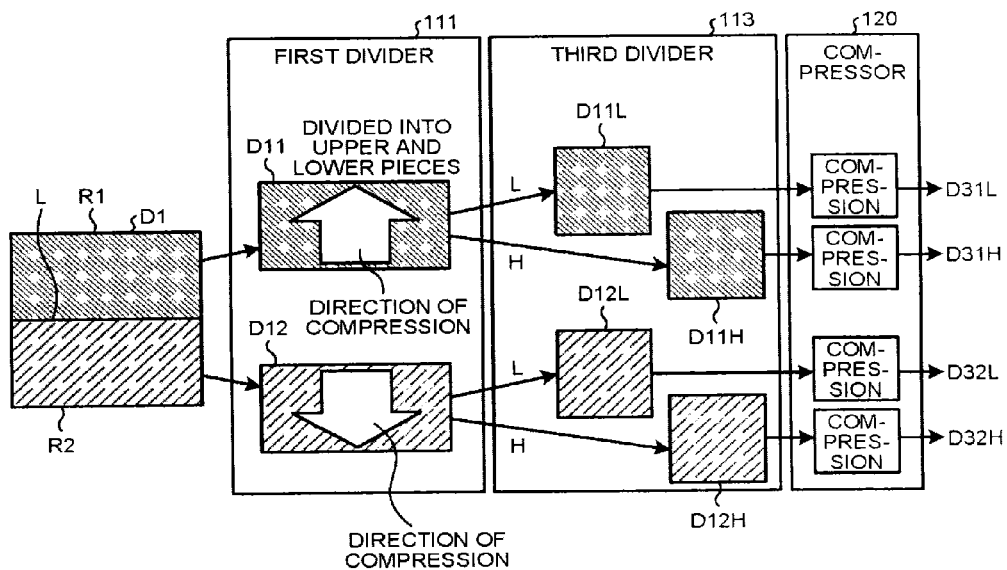
FIG. 17 is a drawing for explaining division and compression of projection data.

FIG. 17 is a drawing for explaining division and compression of the projection data D1. As illustrated in FIG. 17, the third divider 113 divides the pieces of divided data D11 and D12 resulting from the division by the first divider 111 into pieces of divided data D11L, D11H, D12L, and D12H, by performing a frequency conversion process such as a Discrete Cosine Transform (DCT) or a wavelet process on the pieces of divided data D11 and D12 and dividing the data in correspondence with the mutually-different frequency bands (in the present example, a one-dimensional wavelet process is performed in a horizontal direction so as to divide the data into a low-frequency component and a high-frequency component in correspondence with the frequency bands), so as to increase the number of divided pieces up to four. In other words, the third divider 120 uses a wavelet transformation to divide the first data group into multiple different frequency bands, and uses a wavelet transformation to divide the second data group into multiple different frequency bands.

The compressor 120 generates and outputs pieces of compressed data D31L, D31H, D32L, and D32H, by compressing the pieces of divided data D11L, D11H, D12L, and D12H resulting from the division by the third divider 113, sequentially starting with the dividing line L side, in the direction away from the dividing line L.

As explained above, when the number of divided pieces is increased, it is possible to realize an embodiment by combining the dividing process corresponding to the mutually-different frequency bands. As for the frequency conversion process, it is acceptable to use any of various types of frequency conversion methods such as the DCT or a wavelet process. As for the direction and the dimension of the conversion, it is acceptable to use any of various types such as horizontal one-dimensional, vertical one-dimensional, or horizontal/vertical two-dimensional. The division of frequency bands may be with a division number of more than two. It is also acceptable to perform the frequency conversion process a plurality of times successively.

When the compressing process is performed, it is expected that an advantageous effect is achieved where the correlation between adjacently-positioned pixels becomes higher due to the frequency conversion. It is therefore also possible to expect an advantageous effect where compressive strains are reduced due to enhanced encoding efficiency. It is also acceptable to assign mutually-different encoding amounts in correspondence with the mutually-different frequency bands, in accordance with the divided frequency bands. In other words, the compressor 120, for example, compresses pieces of divided data corresponding to mutually-different frequency bands that are divided into by the third divider, by assigning mutually-different encoding amounts to the mutually-different frequency bands. For example, if it is easier to compress the high-frequency component than to compress the low-frequency component, it is possible to reduce the compressive strains by assigning a larger encoding amount to the low-frequency component than to the high-frequency component (e.g., by assigning a larger encoding amount for the compression of the divided data D11L than for the compression of the divided data D11H).

Further, when the compressing process is performed through the DPCM process that uses the estimation based on the pixels in the surroundings, it is also acceptable to apply variable-length coding to a bit number expressing information about the estimation directions. In other words, for example, the compressor 150 performs a compression by performing an encoding process that uses an estimation based on one or more pixels positioned in a surrounding of a compression target pixel and performs a variable-length coding process on a bit number expressing information about one or more estimation directions. Due to the frequency conversion, because the correlation between adjacently-positioned pixels becomes higher, the possibility for estimation directions to match becomes higher. Accordingly, by applying the variable-length coding to the bit number expressing the information about the estimation directions, the encoding efficiency is expected to be higher.

Further, for medical images that are expected to be used in diagnosis or the like, there is a demand for extremely high image quality. Accordingly, the compressor 120 implements the Differential Pulse-Code Modulation (DPCM) process that prevents the image quality of the head line from being lowered. Generally speaking, when data is divided and compressed by using an estimation based on adjacently-positioned pixels, the pixel values after the compression are found to be discontinuous because, at the boundary of the division, it is not possible to make an estimation across the boundary. The image quality of the reconstructed image is therefore degraded. To cope with this situation, when the compressing process is performed after the dividing process corresponding to the frequency bands as described in the third embodiment, it is possible to inhibit the image quality degradation caused by the division, because theoretically the discontinuity at the boundary of the division cannot occur, and the reconstructed projection data D2 therefore has no discontinuity.

Figure 18:
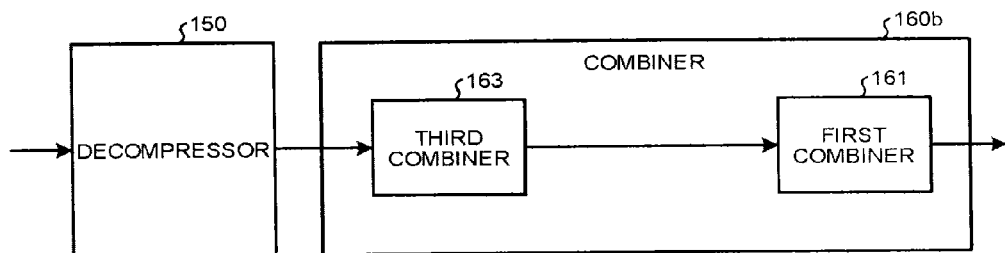
FIG. 18 is a diagram of a decompressor and a combiner according to the third embodiment.

FIG. 18 is a diagram of the decompressor 150 and a combiner 160b according to the third embodiment. As illustrated in FIG. 18, the combiner 160b includes, prior to the first combiner 161, a third combiner 163 configured to combine together pieces of data decompressed by the decompressor 150.

Figure 19:
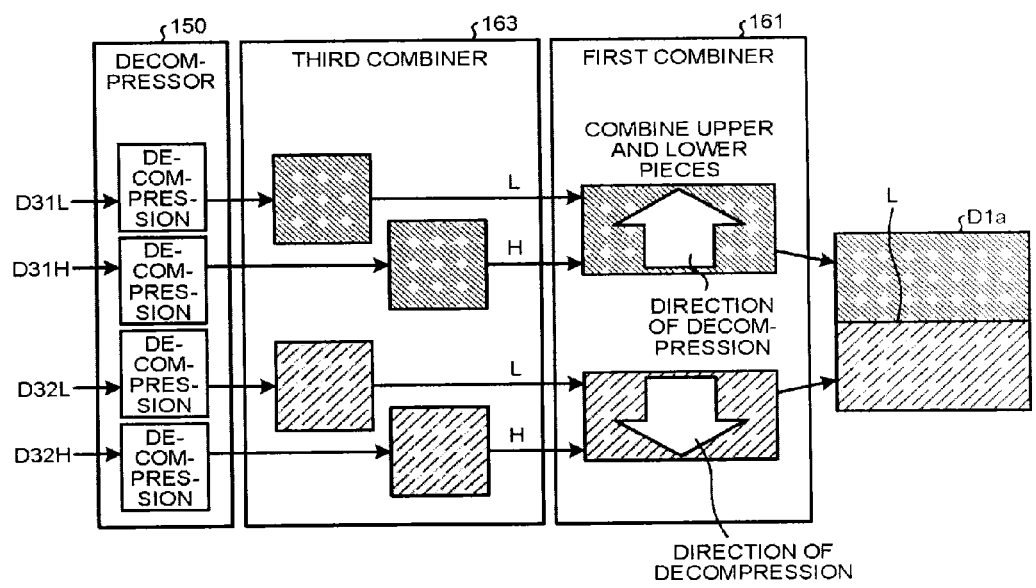
FIG. 19 is a drawing for explaining decompression and combining of compressed data.

FIG. 19 is a drawing for explaining decompression and combining of the pieces of compressed data D31L, D31H, D32L, and D32H. As illustrated in FIG. 19, the pieces of compressed data D31L, D31H, D32L, and D32H are each decompressed by the decompressor 150. In other words, for example, the decompressor 150 decompresses pieces of data each of which each of a plurality of divided first data is compressed into, to obtain a plurality of third decompressed data, the first data group has been divided into the plurality of divided first data each of which corresponding to mutually-different frequency bands, and decompresses pieces of data each of which each of a plurality of divided second data is compressed into, to obtain a plurality of fourth decompressed data, the second data group has been divided into the plurality of divided second data each of which corresponding to mutually-different frequency bands. More specifically, similarly to the compressing processes, the pieces of data are sequentially decompressed starting with the dividing line L side, in the direction away from the dividing line L.

The third combiner 163 is configured to combine four pieces of divided data into two pieces of divided data, by performing a combining process and a time conversion process an inverse conversion of the frequency conversion) on the pieces of data corresponding to the frequency bands that were decompressed by the decompressor 150. In other words, the third combiner 163 combines together the plurality of third decompressed data at different frequency bands and performs a conversion process into a time domain, to obtain the first decompressed data, and combines together the plurality of fourth decompressed data at different frequency bands and performs a conversion process into a time domain, to obtain the second decompressed data. As a result, the third combiner 163 obtains the pieces of data corresponding to the upper area R1 and the lower area R2. In the third embodiment, the time conversion (a one-dimensional inverse wavelet process in a horizontal direction) is performed on the low-frequency component and the high-frequency component in correspondence with the frequency bands. In this situation, the time conversion process needs to be an inverse conversion of the frequency conversion performed by the compressor.

The first combiner 161 generates and outputs the projection data D1a by combining together the pieces of data (the pieces of data corresponding to the upper area R1 and the lower area R2) resulting from the combining process by the third combiner 163 so as to fit each other at the dividing line L. More specifically, the first combiner 161 sequentially combines the pieces of decompressed data in such a manner that, when the decompressing processes were sequentially performed starting with the lines that are in contact with the dividing line L, the last line of the data resulting from the decompression with respect to the area R1 and the last line of the data resulting from the decompression with respect to the area R2 are combined last. Because of this arrangement, the projection data D1a obtained as a result of the combining process has the same positional arrangement of data, as the projection data D1 before the compression.

Fourth Embodiment

Figure 20:
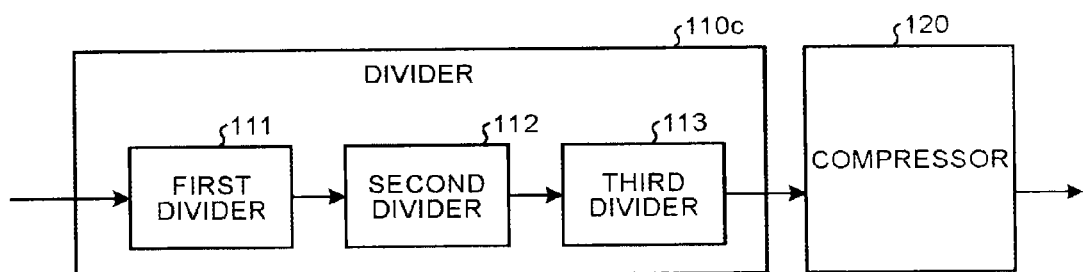
FIG. 20 is a diagram of a divider and a compressor according to a fourth embodiment.

FIG. 20 is a diagram of a divider 110c and the compressor 120 according to a fourth embodiment. As illustrated in FIG. 20, in the fourth embodiment, the divider 110c includes the second divider 112 and the third divider 113, subsequently to the first divider 111.

Figure 21:
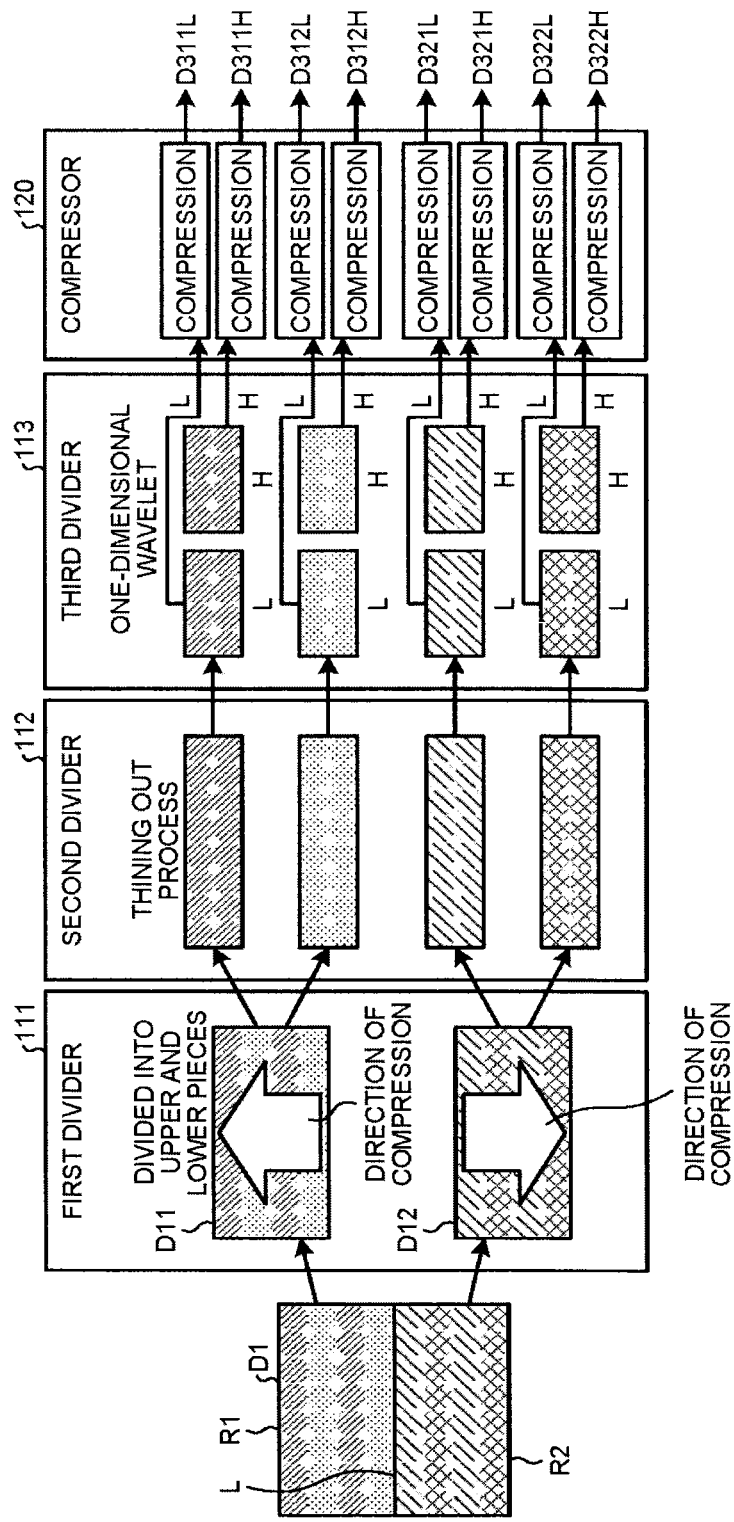
FIG. 21 is a drawing for explaining division and compression of projection data.

FIG. 21 is a drawing for explaining division and compression of the projection data D1. As illustrated in FIG. 21, the second divider 112 increases the number of divided pieces up to four, by alternately thinning out parts of the pieces of divided data D11 and D12 resulting from the division by the first divider 111. Subsequently, the third divider 113 divides the pieces of data resulting from the division by the second divider 112 into pieces of compressed data D311L, D311H, D312L, D312H, D321L, D321H, D322L, and D322H by dividing the data into a plurality of pieces in correspondence with mutually-different frequency bands, so as to increase the number of divided pieces up to eight. When the number of divided pieces is increased in this manner, it is possible to realize an embodiment by combining the division in which parts of the detection data (the pixels) are thinned out alternately, with the dividing process corresponding to the mutually-different frequency bands.

For medical images that are expected to be used in diagnosis or the like, there is a demand for extremely high image quality. For this reason, the compressor 120 implements the Differential Pulse-Code Modulation (DPCM) process that prevents the image quality of the head line from being lowered. Generally speaking, when data is divided and compressed by using an estimation based on adjacently-positioned pixels, there is a possibility that the pixel values after the compression may be discontinuous because, at the boundary of the division, it is not possible to make an estimation across the boundary. The image quality of the reconstructed image is therefore degraded. To cope with this situation, by performing the compressing process after the dividing process with the interleaving processing and the dividing process corresponding to the frequency bands are performed as described in the fourth embodiment, it is possible to reduce the discontinuity at the boundary of the division. Accordingly, because it is possible to reduce discontinuity in the reconstructed projection data D2, it is possible to inhibit the image quality degradation caused by the division.

Figure 22:
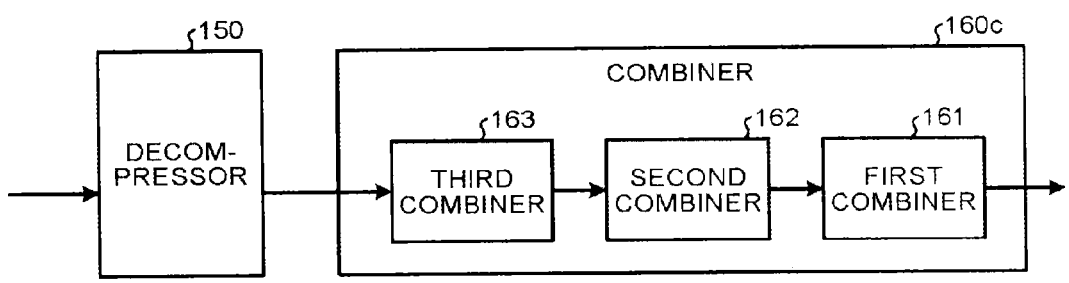
FIG. 22 is a diagram of a decompressor and a combiner according to the fourth embodiment.

FIG. 22 is a diagram of the decompressor 150 and a combiner 160c according to the fourth embodiment. As illustrated in FIG. 22, the combiner 160c includes, prior to the first combiner 161, the third combiner 163 and the second combiner 162 configured to combine pieces of data decompressed by the decompressor 150.

Figure 23:
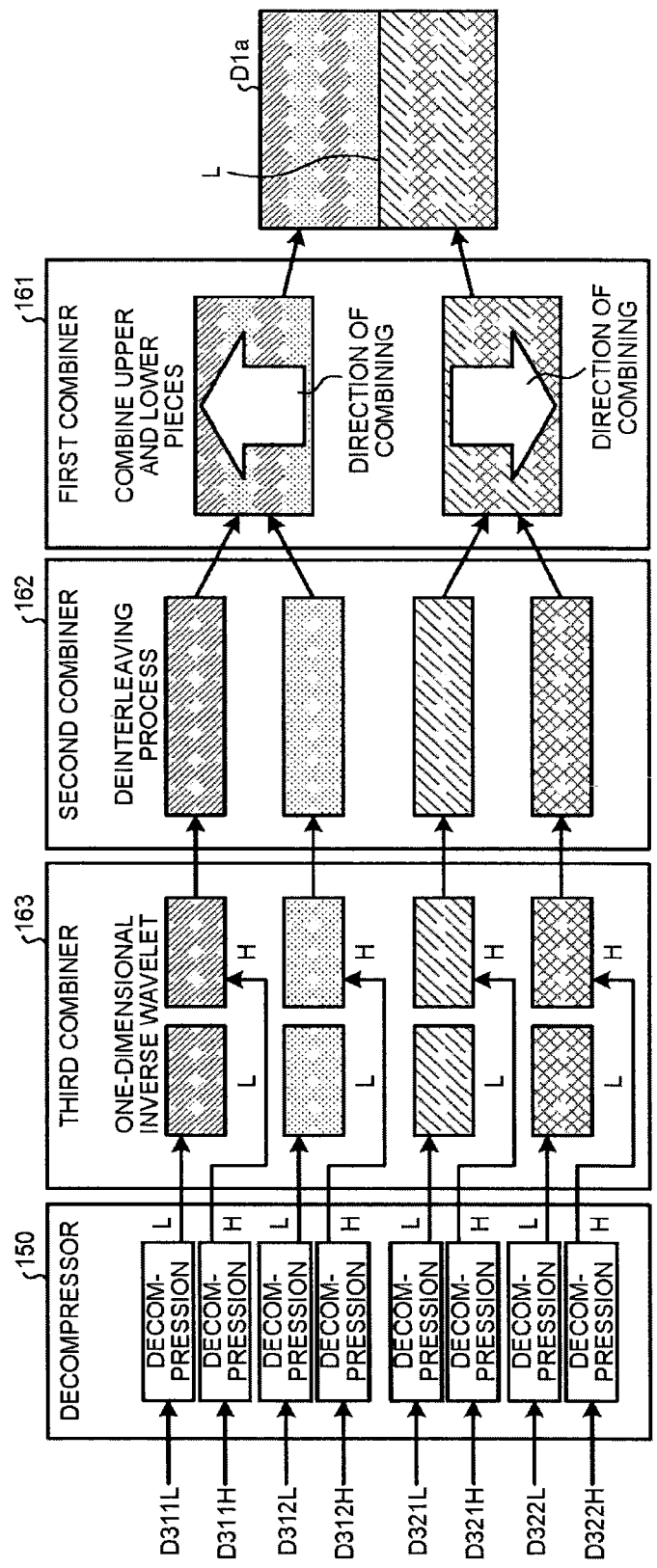
FIG. 23 is a drawing for explaining decompression and combining of compressed data.

FIG. 23 is a drawing for explaining decompression and combining of the pieces of compressed data D311L, D311H, D312L, D312H, D321L, D321H, D322L, and D322H. As illustrated in FIG. 23, the pieces of compressed data D311L, D311H, D312L, D312H, D321L, D321H, D322L, and D322H are each decompressed by the decompressor 150. More specifically, similarly to the compressing processes, the pieces of data are sequentially decompressed starting with the dividing line L side, in the direction away from the dividing line L.

The third combiner 163 is configured to combine eight pieces of divided data into four pieces of divided data by performing a combining process and a time conversion process (an inverse conversion of the frequency conversion) on the pieces of data corresponding to the frequency bands that were decompressed by the decompressor 150. Subsequently, the second combiner 162 combines the four pieces of divided data into two pieces of divided data by performing a deinterleaving processing on the four pieces of divided data resulting from the combining process performed by the third combiner 163. As a result, the pieces of data corresponding to the upper area R1 and the lower area R2 are obtained.

The first combiner 161 generates and outputs the projection data D1a, by combining together the pieces of data (the pieces of data corresponding to the upper area R1 and the lower area R2) resulting from the combining process by the second combiner 162 so as to fit each other at the dividing line L. More specifically, the first combiner 161 sequentially combines the pieces of decompressed data, in such a manner that, when the decompressing processes were sequentially performed starting with the lines that are in contact with the dividing line L, the last line of the data resulting from the decompression with respect to the area R1 and the last line of the data resulting from the decompression with respect to the area R2 are combined last. Because of this arrangement, the projection data D1a obtained as a result of the combining process has the same positional arrangement of data, as the projection D1 before the compression.

Fifth Embodiment

Figure 24:
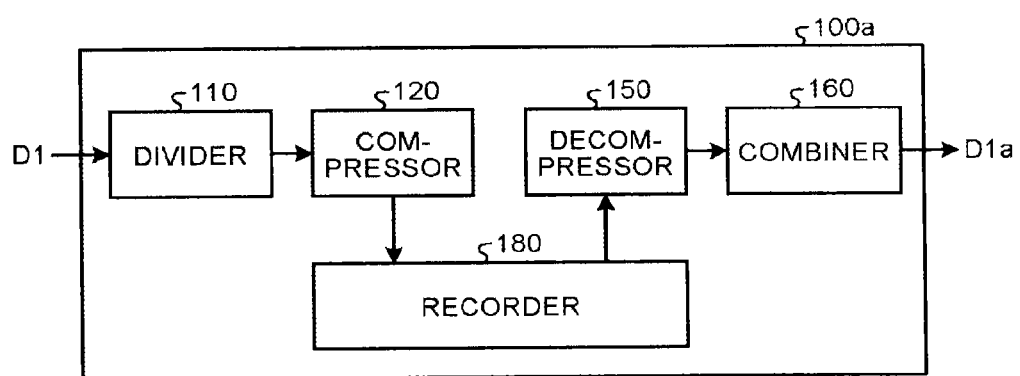
FIG. 24 is a diagram of a medical image processor according to a fifth embodiment.

FIG. 24 is a diagram of a medical image processor 100a according to a fifth embodiment. As illustrated in FIG. 24, in addition to the divider 110, the compressor 120, the decompressor 150, and the combiner 160, the medical image processor 100a includes a recorder 180 configured to record the compressed data obtained by the compressor 120 into a storage device such as a Hard Disk Drive (HDD).

The recorder 180 is configured to record, together with the compressed data, information about the compressing process performed by the compressor 120 (e.g., whether the data is divided by performing an interleaving processing or not, whether the data is divided in correspondence with frequency bands or not, information required by an inverse conversion of the frequency conversion, information required by a deinterleaving processing that makes a matching pair with the interleaving processing), as additional information. For example, the information may be recorded as additional information that is compliant with Digital Imaging and COmmunication in Medicine (DICOM) standards. The decompressor 150 reads the compressed data and the additional information recorded by the recorder 180 and decompresses the compressed data so as to be consistent with the additional information.

Further, not only in the storage device provided therewith, the recorder 180 may connect, via a communication interface, to a storage device connected to a network such as a Local Area Network (LAN) and may transfer and record the compressed data obtained by the compressor 120 into the storage device.

As explained in the fifth embodiment, the present disclosure is applicable to a situation where data pertaining to a medical image such as the projection data D1 is compressed and recorded into a storage device. In that situation, it is possible to compress and record the data pertaining to the medical image while inhibiting the image quality deterioration and to make a contribution to a cost reduction of the entire apparatus by reducing the size of the stored data. Further, when the recorded data is read and browsed, it is possible to restore and display an image having a high level of precision.

The medical image processor 100a is applicable not only to an X-ray CT apparatus handling the projection data D1, but also to other information processing apparatuses such as a workstation (WS) that performs various types of processing on medical images. More specifically, the functional units (e.g., the divider 110, the compressor 120, the decompressor 150, the combiner 160, the recorder 180, and the like) are realized as a result of a computer program (hereinafter, "program") being executed by a Central Processing Unit (CPU) of such an information processing apparatus. Further, the present disclosure is also applicable to other apparatuses such as a Magnetic Resonance imaging (MRI) apparatus, as long as the apparatus is required to perform dividing and compressing processes to realize high image quality of medical images.

Sixth Embodiment

Figure 25:
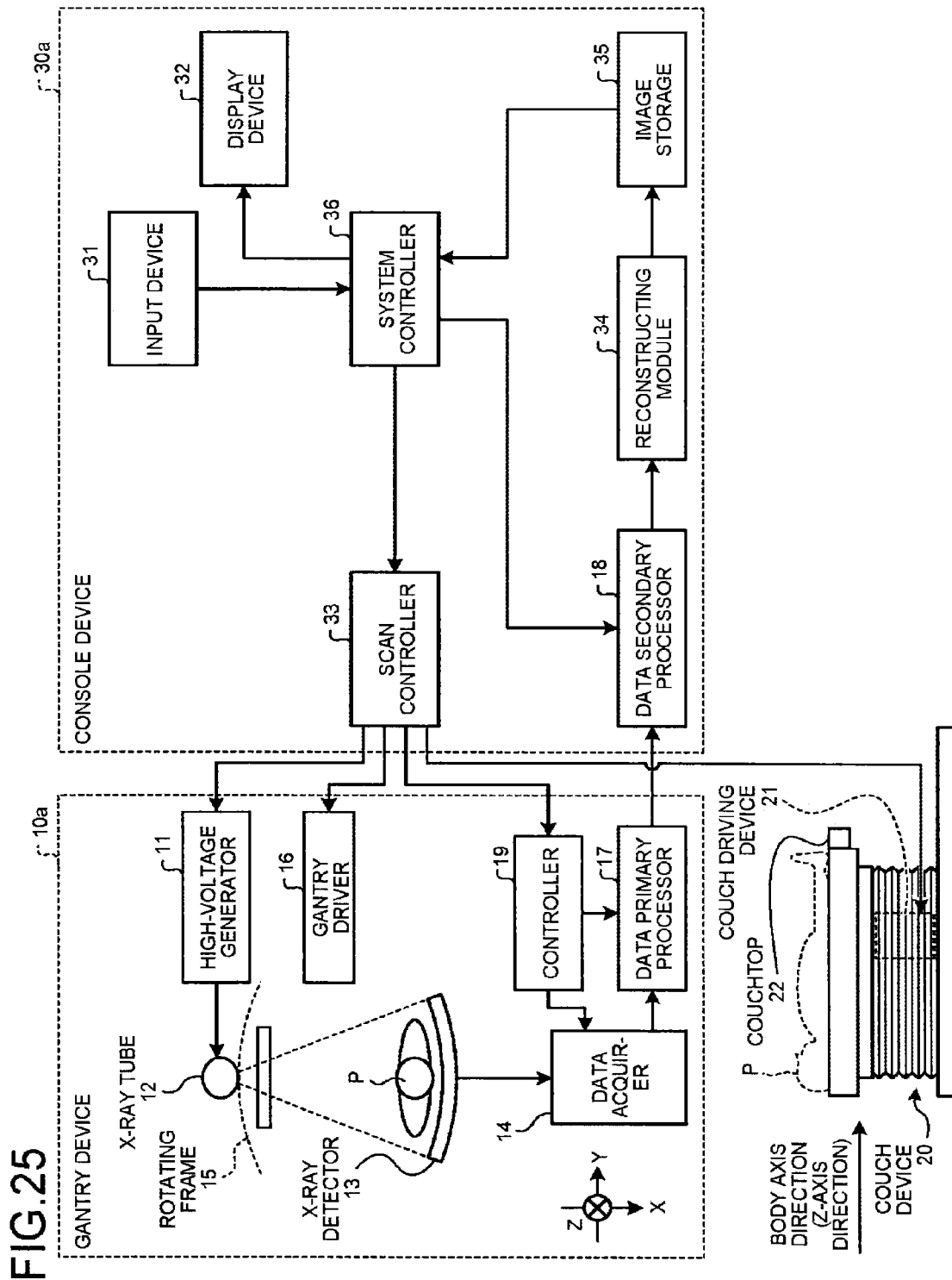
FIG. 25 is an overall diagram of an X-ray CT apparatus according to a sixth embodiment.

FIG. 25 is an overall diagram of an X-ray CT apparatus according to a sixth embodiment. As illustrated in FIG. 25, the X-ray CT apparatus according to the sixth embodiment is configured to reconstruct the projection data D2 by transferring the projection data D1 acquired by the X-ray detector 13 provided for the rotating frame 15 to the data primary processor 17 through an electro-static coupling data communication and further sending the data from the data primary processor 17 to the data secondary processor 18 provided on the console device 30 side via a broadband transmission path.

The transfer module 130 included in the data primary processor 17 is configured to perform a parallel-serial conversion and to perform an optical fiber transmission to the data secondary processor 18. The parallel-serial conversion and communication mechanisms that employ many optical component parts for optical fiber transmissions are extremely expensive. In addition, delays in the transmission that are caused by signal processing processes including the parallel-serial conversion are not negligible, either. In this regard, the compression of the projection data D1 according to the sixth embodiment implements a method suitable for reduction of the data transfer bandwidth used in the transfer of the projection data D1. It is therefore possible to make a contribution to a cost reduction of the entire apparatus.

Further, in the first to the sixth embodiments described above, the examples in which the present disclosure is applied to the projection data D1 are explained; however, it is also acceptable to apply the present disclosure to data related to a medical image (e.g., a tomography image, volume data, or the like) other than the projection data D1. For example, in a situation where reconstructed image data is supplied as an input, it is possible to perform the compressing, transferring, and storing processes on the data at any of the various processing stages of an X-ray CT apparatus.

Figure 26:
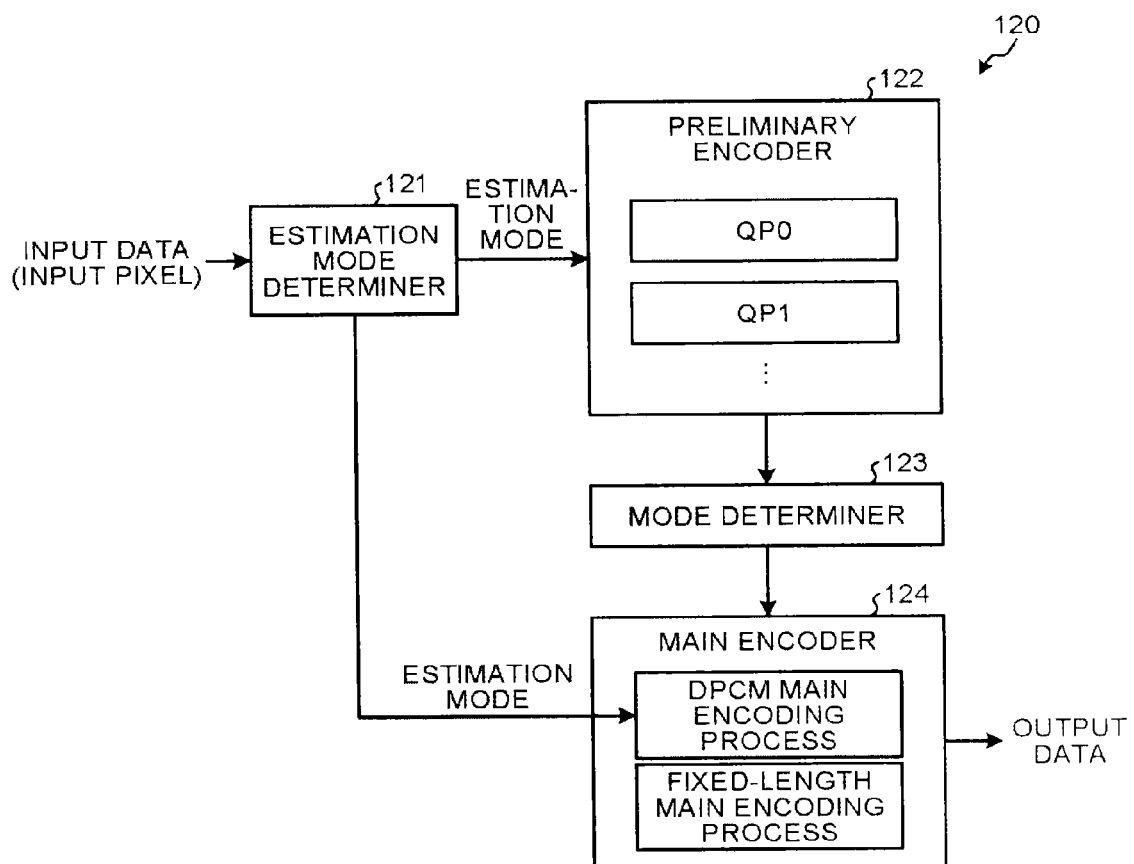
FIG. 26 is a drawing for explaining an outline of an encoding process.
Figure 27:
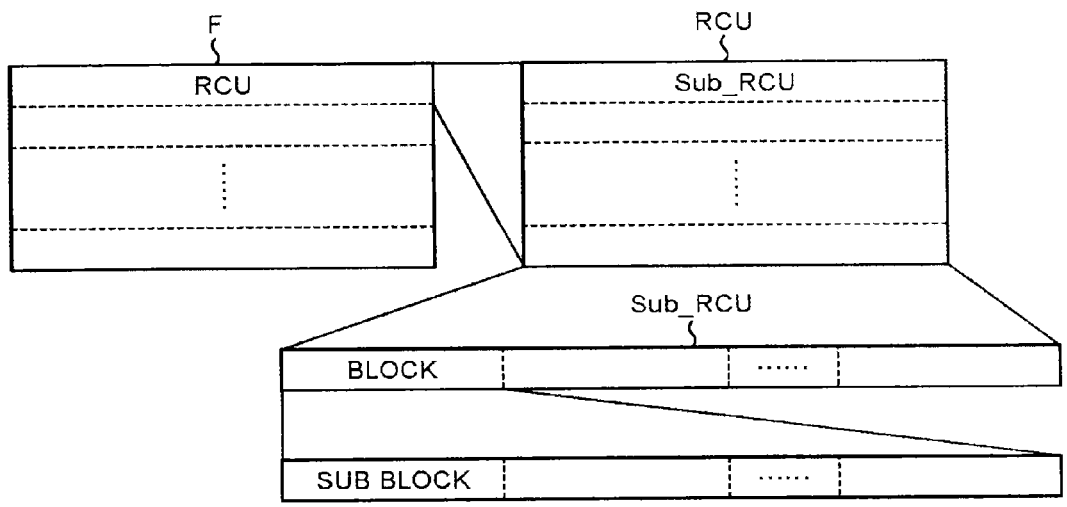
FIG. 27 is a drawing for explaining units of processing.
Figure 28:
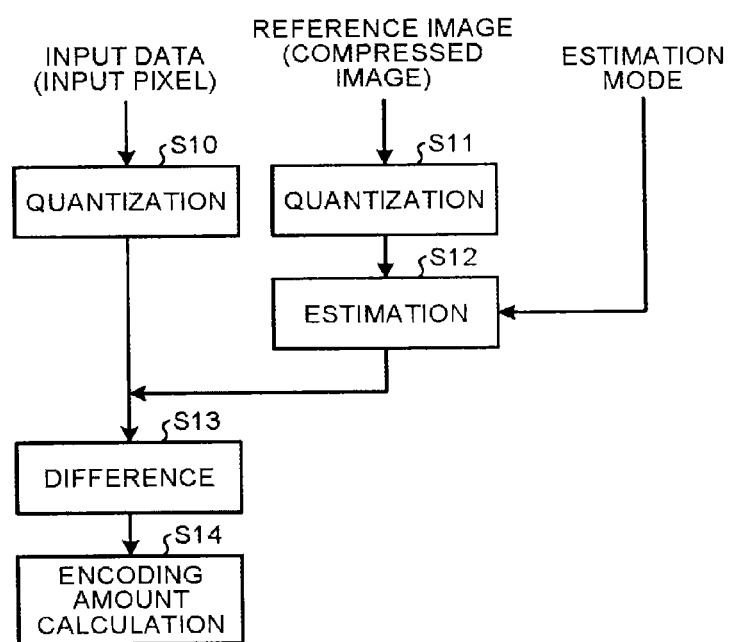
FIG. 28 is a drawing for explaining an outline of a preliminary encoder.
Figure 29:
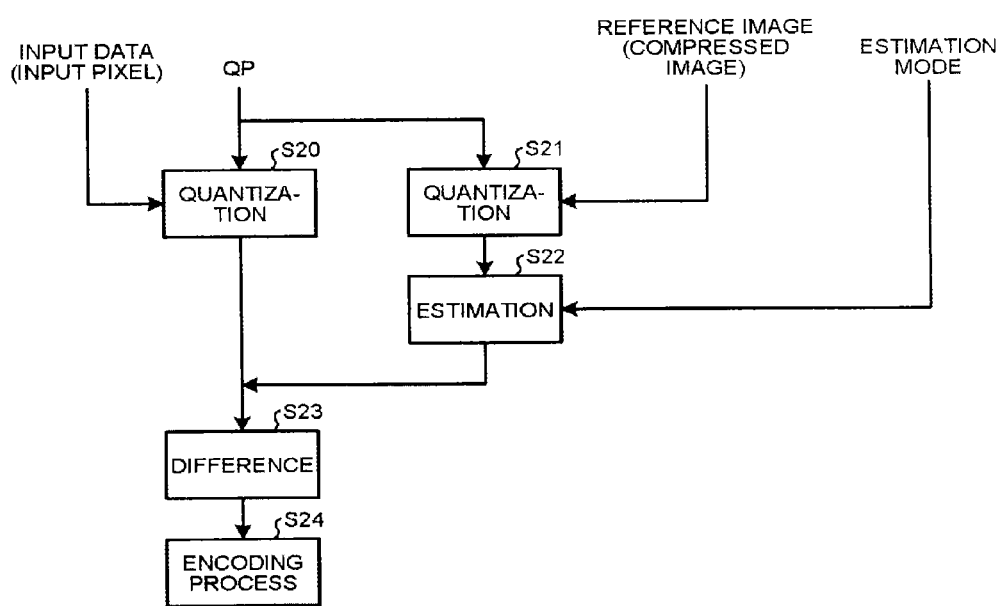
FIG. 29 is a drawing for explaining a main encoding process.

Next, details of an encoding process (a compressing process) in the first to the sixth embodiments will be explained. FIG. 26 is a drawing for explaining an outline of the encoding process. FIG. 27 is a drawing for explaining units of processing. FIG. 28 is a drawing for explaining an outline of a preliminary encoder. FIG. 29 is a drawing for explaining an outline of a main encoder.

As illustrated in FIG. 26, the compressor 120 includes an estimation mode determiner 121, a preliminary encoder 122, a mode determiner 123, and a main encoder 124. Input data (an input pixel) that has been input to the compressor 120 is eventually encoded by the main encoder 124 and output as output data.

The estimation mode determiner 121 is configured to determine, with respect to the input data, an estimation mode used for calculating a pixel difference, for each of specific minimum processors. More specifically, as illustrated in FIG. 27, a frame/sub-frame F serving as the input data is divided into RCUs. The RCUs are units for which the rate is guaranteed. For example, each of the RCUs is divided in the vertical direction, for example, into sub_RCUs corresponding to lines. Each of the sub_RCUs is divided in the horizontal direction into blocks, and each of the blocks is further divided into sub blocks.

The estimation mode determiner 121 determines an estimation mode in units of sub blocks, by using the sub blocks in the frame/sub-frame F as the minimum processors. The estimation mode is selected from among the following four types: Left, Top, DC, and PLANE (see FIG. 5A).

The estimation mode determiner 121 determines the estimation mode by selecting an estimation mode that makes the Sum of Absolute Differences (SAD) the smallest for each of the sub blocks, by using the input pixel. The estimation mode determined by the estimation mode determiner 121 is sent to the preliminary encoder 122 and the main encoder 124 in the form of a notification.

The preliminary encoder 122 is configured to calculate an encoding amount for an RCU (rate guaranteed unit) or a sub_RCU by using a QP parallel system. An outline of a preliminary encoder corresponding to one QP among preliminary encoders (QP0, QP1, and so on) that are present in the QP parallel system is illustrated in FIG. 28.

The preliminary encoder first quantizes an input pixel and a reference image (a compressed image used for the estimation) (steps S10 and S11). Subsequently, the preliminary encoder generates an estimated value by using the quantized reference image and the determined estimation mode (step S12) and generates a difference signal by calculating the difference between the estimated value and the quantized input pixel (step S13). After that, the preliminary encoder calculates an encoding amount by applying Golomb-Rice coding or the like to the difference signal (step S14).

The mode determiner 123 determines a main encoding method (either a QP for a DPCM main encoding process or a fixed-length main encoding process) so as to be able to achieve a value smaller than a target encoding amount for the RCU (the rate guaranteed unit) or the sub_RCU. The main encoder 124 encodes the input image and outputs compressed data, by using the estimation mode determined by the estimation mode determiner 121, a code table for the Golomb-Rice coding determined by the preliminary encoder 122, and the QP determined by the mode determiner 123. An outline of the main encoder 124 is illustrated in FIG. 29.

In the main encoder 124, at first, the input pixel and the reference image are quantized by the QP determined by the mode determiner 123 (steps S20 and S21). The quantization is the same as the one performed in the preliminary encoding process. Subsequently, the main encoder 124 generates an estimated value by using the quantized reference image and the estimation mode (step S22). After that, the main encoder 124 obtains a difference signal by calculating the difference between the generated estimated value and the quantized input pixel (step S23). The estimation and the difference are the same as those in the preliminary encoding process. Subsequently, the main encoder 124 encodes the difference signal by using the code table determined in the preliminary encoding process, and mode information (the QP, the code table, and the estimation mode) and the encoded data serve as an output from the main encoder 124 (step S24).

In this situation, to realize a high-speed DPCM process by using the pixel parallel processing in which the quantization, the estimated value generation, and the encoding are performed at the same time for a plurality of input pixels, the position of the quantization is changed. It is, however, acceptable to arrange the position of the quantization to be in another position.

Next, details of a decoding process (the decompressing process) according to the first to the sixth embodiments will be explained. The decompressing process is performed in processors illustrated in FIG. 27 (sub_RCUs, blocks including in each sub_RCU, sub blocks included in each block, and pixels included in each sub block).

Figure 30:
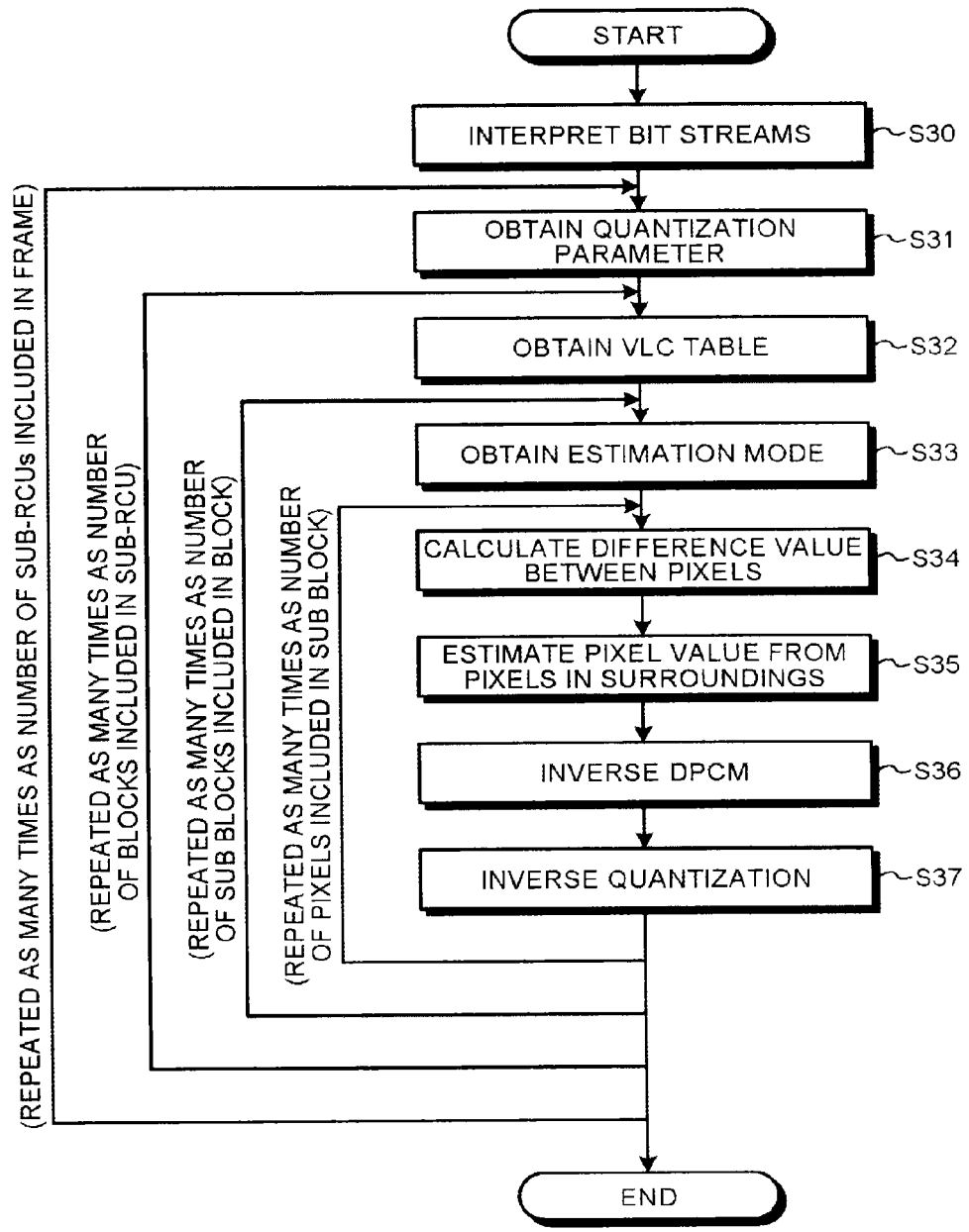
FIG. 30 is a flowchart indicating a decoding method.

FIG. 30 is a flowchart indicating a decoding method. As illustrated in FIG. 30, the decompressor 150 sequentially performs the following processes: interpret bit streams (step S30); obtain a quantization parameter (step S31), obtain a Variable-Length Coding (VLC) table (step S32); obtain an estimation mode (step S33); calculate a difference value between pixels (step S34); estimate a pixel value from pixels in the surroundings (step S35); an inverse DPCM process (step S36); and an inverse quantization process (step S37).

The interpretation of the bit streams is a process of separating the bit streams corresponding to the quantization parameter, the VLC table, the estimation mode, the pixel difference resulting from a VLC process, and the like, so as to provide each of different processing stages with the information. The obtainment of the quantization parameter is a process of obtaining a parameter used for the quantization. For a simple quantization process such as a bit shift, the parameter of the quantization is this shift amount. The VLC table and the estimation mode are obtained by separating the bit streams.

The pixel estimation is performed by using three pixels in the left, top, and upper left positions. The estimation mode is selected from among the following four types: Left, Top, DC, and PLANE (see FIG. 5A). For a stream encoded by performing the Golomb-Rice coding, the difference value between the pixels is calculated from codeword encoded by performing the Golomb-Rice coding. As for the pixel value estimation based on the pixels in the surroundings, a pixel value is estimated by using the three pixels in the left, top, and upper left positions. In the present explanation, the example is used in which the decoding process (the inverse DPCM and the inverse quantization) is performed on the stream on which the variable-length coding process has been performed through the DPCM process. However, to decode a stream that has been encoded by using both a fixed-length coding process and a variable-length coding process, it is determined which encoding process was used between the fixed-length coding process and the variable-length coding process, so that the decoding process is performed by implementing the method described above if the variable-length coding process was used and so that a decoding process is performed by using a decoding method for fixed-length coding if the fixed-length coding process was used.

For the processes at steps S30 through S37 described above, the processes at steps 334 through S37 are repeated as many times as the number of pixels included in the sub block. The processes at steps S33 through S37 are repeated as many times as the number of sub blocks included in the block. The processes at steps S32 through S37 are repeated as many times as the number of blocks included in the sub_RCU. The processes at steps S31 through S37 are repeated as many times as the number of sub_RCUs included in the frame. As a result, the decoding process is performed on the one frame/sub-frame F.

The embodiments described herein may be carried out in a variety of other forms. For example, when an image taking plan used for taking an image of the patient P is input and set by using the input device 31 included in the X-ray CT apparatus, it is acceptable to change, under the control of the system controller 36, settings as to whether the dividing process is performed or not and the contents of the dividing process performed by the divider 110, in accordance with the set image taking plan. For example, if an image taking plan is set so as to perform an image taking process having a width equal to or larger than a predetermined value in the slice direction of the X-ray detector 13, it is necessary to transfer and process a large amount of projection data D1 in a real-time manner. Thus, when an image taking plan that requires the transfer of a large amount of projection data D1 in a real-time manner is set, it is acceptable to switch the mode from a normal mode without the dividing process to a dividing mode with the dividing process, so that the projection data D1 is divided into two pieces by the first divider 111.

Further, it is also acceptable to change the dividing mode by selecting from among multiple options according to the data amount of the projection data D1. For example, if the data amount of the projection data D1 is equal to or larger than a predetermined value, it is acceptable to switch the mode to, not only the mode (a first dividing mode) in which the projection data D1 is divided into two pieces by the first divider 111, but also to another dividing mode (a second dividing mode) in which at least one of the second divider 112 and the third divider 113 is employed, so as to increase the number of divided pieces.

More specifically, it is acceptable to prepare, in advance, a plurality of sets each made up of any of the dividers 110, 110a, 110b, and 110c and any of the combiners 160, 160a, 160b, and 160c that corresponds thereto, so that the system controller 36 changes the employed set whose number of divided pieces becomes increased, if a large amount of projection data D1 needs to be transferred and processed in a real-time manner.

For example, if an image taking process is performed by using a width smaller than a predetermined threshold value in the slice direction of the X-ray detector 13, the mode is switched to the first dividing mode that employs the set made up of the divider 110 and the combiner 160 configured to divide the projection data D1 into two pieces, to compress and transfer the data, and to restore the data. In contrast, if an image taking process is performed by using a width that is equal to or larger than the predetermined threshold value in the slice direction of the X-ray detector 13, the mode is switched to the second dividing mode that employs a set made up of the divider 110a and the combiner 160a or a set made up of the divider 110b and the combiner 160b configured to divide the projection data D1 into four pieces, to compress and transfer the data, and to restore the data. In another example, if the width is even larger, the mode is switched to a third dividing mode that employs a set made up of the divider 110c and the combiner 160c configured to divide the projection data D1 into eight pieces, to compress and transfer the data, and to restore the data.

The switching among the dividers 110, 110a, 110b, and 110c and among the combiners 160, 160a, 160b, and 160c may be realized with a dynamic reconstruction of a Field Programmable Gate Array (FPGA). Further, the switching described above may be implemented on the basis of not only the width in the slice direction of the X-ray detector 13, but also the width in the channel direction or the frame rate.

Furthermore, the constituent elements of the apparatuses and the devices that are shown in the drawings are based on functional concepts. Thus, it is not necessary to physically configure the elements as indicated in the drawings. In other words, the specific mode of distribution and integration of the apparatuses and the devices is not limited to the ones shown in the drawings. It is acceptable to functionally or physically distribute or integrate all or a part of the apparatuses and the devices in any arbitrary units, depending on various loads and the status of use. Furthermore, all or an arbitrary part of the processing functions performed by the apparatuses and the devices may be realized by a Central Processing Unit (CPU) and a computer program that is analyzed and executed by the CPU or may be realized as hardware using wired logic.

According to at least one aspect of the embodiments described above, it is possible to compress the data pertaining to the medical image while inhibiting the image quality deterioration.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
   compressing circuitry configured to compress, for each of a first data group and a second data group both of which being included in data pertaining to a medical image, each of the first data group and the second data group separately, starting from data corresponding to a boundary between the first data group and the second data group and shifting sequentially in a direction away from the boundary, wherein the compressing circuitry is configured to adjust or select the boundary between the first data group and the second data group based on imaging plan information corresponding to the data pertaining to the medical image, and when imaging information regarding a predetermined region is included in the imaging plan information corresponding to the data pertaining to the medical image data, the compressing circuitry is configured to specify the first data group and the second data group such that the boundary between the first data group and the second data group becomes perpendicular to a channel direction of an X-ray detector that detects the data pertaining to the medical image data.

2. The medical image processing apparatus according to claim 1, wherein
the data pertaining to the medical image is X-ray detection data that is obtained from an X-ray detector and that is obtained for each view that corresponds to a predetermined angle of an X-ray tube.

3. The medical image processing apparatus according to claim 1, further comprising:
first dividing circuitry configured to perform a division of the data pertaining to the medical image data into two areas, a dividing line being the boundary and configured to acquire the first data group and the second data group, wherein
the compressing circuitry is configured to compress the first data group and the second data group, starting from the boundary and shifting sequentially in a direction away from the boundary.

4. The medical image processing apparatus according to claim 1, wherein the compressing circuitry is configured to assign a larger encoding amount for compression of data closest to the boundary than encoding amount for compression of other data.

5. The medical image processing apparatus according to claim 1, wherein the compressing circuitry is configured to perform a compression by performing a Differential Pulse-Code Modulation (DPCM) processing.

6. A medical image processing apparatus comprising:
compressing circuitry configured to compress, for each of a first data group and a second data group both of which being included in data pertaining to a medical image, each of the first data group and the second data group separately, starting from data corresponding to a boundary between the first data group and the second data group and shifting sequentially in a direction away from the boundary; and
second dividing circuitry configured to alternately thin out and divide the first data group into a plurality of pieces of data and configured to alternately thin out and divide the second data group into a plurality of pieces of data.

7. A medical image processing apparatus comprising:
compressing circuitry configured to compress, for each of a first data group and a second data group both of which being included in data pertaining to a medical image, each of the first data group and the second data group separately, starting from data corresponding to a boundary between the first data group and the second data group and shifting sequentially in a direction away from the boundary; and
third dividing circuitry configured to divide the first data group into multiple different frequency bands, and configured to divide the second data group into multiple different frequency bands.

8. The medical image processing apparatus according to claim 7, wherein the third dividing circuitry
is configured to use a wavelet transformation to divide the first data group into multiple different frequency bands, and
is configured to use a wavelet transformation to divide the second data group into multiple different frequency bands.

9. The medical image processing apparatus according to claim 7, wherein the compressing circuitry is configured to compress pieces of divided data corresponding to mutually-different frequency bands that are divided into by the third dividing circuitry, by assigning mutually-different encoding amounts to the mutually-different frequency bands.

10. A medical image processing apparatus comprising:
compressing circuitry configured to compress, for each of a first data group and a second data group both of which being included in data pertaining to a medical image, each of the first data group and the second data group separately, starting from data corresponding to a boundary between the first data group and the second data group and shifting sequentially in a direction away from the boundary, wherein
the compressing circuitry
is configured to perform a compression by performing an encoding process that uses an estimation based on one or more pixels positioned in a surrounding of a compression target pixel and
is configured to perform a variable-length coding process on a bit number expressing information about one or more estimation directions.

11. A medical image processing apparatus comprising:
compressing circuitry configured to compress, for each of a first data group and a second data group both of which being included in data pertaining to a medical image, each of the first data group and the second data group separately, starting from data corresponding to a boundary between the first data group and the second data group and shifting sequentially in a direction away from the boundary;
decompressing circuitry
configured to decompress compressed data of the first data group to obtain first decompressed data, and
configured to decompress compressed data of the second data group to obtain second decompressed data; and
first combining circuitry
configured to combine the first decompressed data and the second decompressed data so as to fit each other at a dividing line corresponding to the boundary, wherein
the decompressing circuitry
is configured to decompress pieces of data each of which each of a plurality of divided first data is compressed into, to obtain a plurality of third decompressed data, the first data group having been alternately thinned out and divided into each of the plurality of divided first data, and
is configured to decompress pieces of data each of which each of a plurality of divided second data is compressed into, to obtain a plurality of fourth decompressed data, the second data group having been alternately thinned out and divided into each of the plurality of divided second data, and
the medical image processing apparatus further comprises:
second combining circuitry
configured to alternately combine the plurality of third decompressed data to obtain the first decompressed data, and
configured to alternately combine the plurality of fourth decompressed data to obtain the second decompressed data.

12. A medical image processing apparatus comprising:
compressing circuitry configured to compress, for each of a first data group and a second data group both of which being included in data pertaining to a medical image, each of the first data group and the second data group separately, starting from data corresponding to a boundary between the first data group and the second data group and shifting sequentially in a direction away from the boundary;

decompressing circuitry
configured to decompress compressed data of the first data group to obtain first decompressed data, and
configured to decompress compressed data of the second data group to obtain second decompressed data; and first combining circuitry
configured to combine the first decompressed data and the second decompressed data so as to fit each other at a dividing line corresponding to the boundary, wherein the decompressing circuitry
is configured to decompress pieces of data each of which each of a plurality of divided first data is compressed into, to obtain a plurality of third decompressed data, the first data group has been divided into the plurality of divided first data each of which corresponding to mutually-different frequency bands, and
is configured to decompress pieces of data each of which each of a plurality of divided second data is compressed into, to obtain a plurality of fourth decompressed data, the second data group having been divided into the plurality of divided second data each of which corresponding to mutually-different frequency bands, the medical image processing apparatus further comprises:

third combining circuitry
configured to combine together the plurality of third decompressed data at different frequency bands and configured to perform a conversion process into a time domain, to obtain the first decompressed data, and
configured to combine together the plurality of fourth decompressed data at different frequency bands and configured to perform a conversion process into a time domain, to obtain the second decompressed data.

13. An X-ray CT apparatus comprising:
data acquiring circuitry configured to obtain projection data by acquiring X-ray detection data obtained by detecting X-rays that have passed through a subject;
compressing circuitry configured to compress, for each of a first data group and a second data group both of which being included in the projection data, each of the first data group and the second data group separately to obtain pieces of compressed projection data, starting from data corresponding to a boundary between the first data group and the second data group and shifting sequentially to a direction away from the boundary;
transfer module circuitry configured to transfer the pieces of compressed projection data;
decompressing circuitry configured to decompress the pieces of projection data that have been transferred thereto by the transfer module circuitry; and
reconstructing circuitry configured to reconstruct a tomography image of the subject on a basis of the decompressed pieces of projection data, wherein the compressing circuitry is configured to adjust or select the boundary between the first data group and the second data group based on imaging plan information corresponding to the data pertaining to the medical image, and when imaging information regarding a predetermined region is included in the imaging plan information corresponding to the data pertaining to the medical image data, the compressing circuitry is configured to specify the first data group and the second data group such that the boundary between the first data group and the second data group becomes perpendicular to a channel direction of an X-ray detector that detects the data pertaining to the medical image data.

14. The X-ray CT apparatus according to claim 13, wherein the projection data is X-ray detection data that is obtained from an X-ray detector and that is obtained for each view that corresponds to a predetermined angle of an X-ray tube.

15. An X-ray CT apparatus comprising:
data acquiring circuitry configured to obtain projection data by acquiring X-ray detection data obtained by detecting X-rays that have passed through a subject;
compressing circuitry configured to compress, for each of a first data group and a second data group both of which being included in the projection data, each of the first data group and the second data group separately to obtain pieces of compressed projection data, starting from data corresponding to a boundary between the first data group and the second data group and shifting sequentially in a direction away from the boundary;
second dividing circuitry configured to alternately thin out and divide the first data group into a plurality of pieces of data and configured to alternately thin out and divide the second data group into a plurality of pieces of data;
transfer module circuitry configured to transfer the pieces of compressed projection data;
decompressing circuitry configured to decompress the pieces of projection data that have been transferred thereto by the transfer module circuitry; and
reconstructing circuitry configured to reconstruct a tomography image of the subject on a basis of the decompressed pieces of projection data.

16. An X-ray CT apparatus comprising:
data acquiring circuitry configured to obtain projection data by acquiring X-ray detection data obtained by detecting X-rays that have passed through a subject;
compressing circuitry configured to compress, for each of a first data group and a second data group both of which being included in the projection data, each of the first data group and the second data group separately to obtain pieces of compressed projection data, starting from data corresponding to a boundary between the first data group and the second data group and shifting sequentially in a direction away from the boundary;
third dividing circuitry configured to divide the first data group into multiple different frequency bands, and configured to divide the second data group into multiple different frequency bands;
transfer module circuitry configured to transfer the pieces of compressed projection data;
decompressing circuitry configured to decompress the pieces of projection data that have been transferred thereto by the transfer module circuitry; and
reconstructing circuitry configured to reconstruct a tomography image of the subject on a basis of the decompressed pieces of projection data.

17. An X-ray CT apparatus comprising:
data acquiring circuitry configured to obtain projection data by acquiring X-ray detection data obtained by detecting X-rays that have passed through a subject;

compressing circuitry configured to compress, for each of a first data group and a second data group both of which being included in the projection data, each of the first data group and the second data group separately to obtain pieces of compressed projection data, starting from data corresponding to a boundary between the first data group and the second data group and shifting sequentially in a direction away from the boundary;

transfer module circuitry configured to transfer the pieces of compressed projection data;

decompressing circuitry configured to decompress the pieces of projection data that have been transferred thereto by the transfer module circuitry;

reconstructing circuitry configured to reconstruct a tomography image of the subject on a basis of the decompressed pieces of projection data, wherein the compressing circuitry is configured to perform a compression by performing an encoding process that uses an estimation based on one or more pixels positioned in a surrounding of a compression target pixel and is configured to perform a variable-length coding process on a bit number expressing information about one or more estimation directions.

* * * * *